US012791552B2

(12) United States Patent
Youngblood et al.

(10) Patent No.: US 12,791,552 B2
(45) Date of Patent: Nov. 10, 2026

(54) T CELL GENE EXPRESSION ANALYSIS FOR USE IN T CELL THERAPIES

(71) Applicant: ST. JUDE CHILDREN'S RESEARCH HOSPITAL, INC., Memphis, TN (US)

(72) Inventors: Benjamin Youngblood, Memphis, TN (US); Jeremy Crawford, Memphis, TN (US); Yiping Fan, Memphis, TN (US); Caitlin Zebley, Memphis, TN (US); Stephen Gottschalk, Germantown, TN (US); Giedre Krenciute, Memphis, TN (US); Christopher Petersen, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 1225 days.

(21) Appl. No.: 17/608,079

(22) PCT Filed: Apr. 8, 2020

(86) PCT No.: PCT/US2020/027291

§ 371 (c)(1),
(2) Date: Nov. 1, 2021

(87) PCT Pub. No.: WO2020/222987

PCT Pub. Date: Nov. 5, 2020

(65) Prior Publication Data

US 2022/0326216 A1 Oct. 13, 2022

Related U.S. Application Data

(60) Provisional application No. 62/842,260, filed on May 2, 2019.

(51) Int. Cl.

| | |
|---|---|
| ***G01N 33/50*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C12N 5/0783*** | (2010.01) |

(52) U.S. Cl.

CPC ............ *G01N 33/505* (2013.01); *A61K 40/11* (2025.01); *A61K 40/31* (2025.01); *A61K 40/4205* (2025.01); *C07K 14/705* (2013.01); *C12N 5/0636* (2013.01); *G01N 33/5023* (2013.01); *A61K 2239/28* (2023.05); *C12Y 201/01037* (2013.01)

(58) Field of Classification Search

None

See application file for complete search history.

(56) References Cited

U.S. PATENT DOCUMENTS

2014/0364434 A1* 12/2014 Daeman ............... C12Q 1/6886 506/8
2017/0306416 A1* 10/2017 Bedoya ................ G01N 33/574
2018/0170992 A1 6/2018 Balyasnikova et al.
2018/0318350 A1* 11/2018 Ahmed ................ C12N 5/0638
2018/0362927 A1 12/2018 Blazar et al.

FOREIGN PATENT DOCUMENTS

WO 2015/142675 A2 9/2015
WO 2017/079642 A1 5/2017
WO 2017079622 A1 5/2017
WO 2018038945 A1 3/2018

OTHER PUBLICATIONS

Feng W, et al., "Analysis method of epigenetic DNA methylation to dynamically investigate the functional activity of transcription factors in gene expression", BMC Genomics. Oct. 5, 2012:13:532. (Year: 2012).*
GEO Accession Viewer (downloaded from the Internet Nov. 1, 2024 at https://www.ncbi.nlm.nih.gov/geo/query/acc.cgi?acc=GPL570). (Year: 2003).*
Communication (International Search Report) issued by the International Searching Authority in International Application No. PCT/US20/27291 dated Jul. 15, 2020, 5 pages total.
Communication (Written Opinion) issued by the International Searching Authority in International Application No. PCT/US20/27291 dated Jul. 15, 2020, 9 pages total.
Derenzo, C. et al., "Genetic Modification Strategies to Enhance CAR T Cell Persistence for Patients with Solid Tumors" Frontiers in Immunology (2019) vol. 10, Article 218, pp. 1-8.
Ghoneim, Hazem E., et al., "De Novo Epigenetic Programs Inhibit PD-1 Blockade-Mediated T Cell Rejuvenation" Cell 170, http://dx.coi.org/10.1016/j.cell.2017.06.007; Jun. 29, 2017, pp. 142-157.
Hitching, L., "There's Just Something About Them: Predicting Response to CAR T Cell Therapy" ACIR Weekly Digest (2018) 3 pages total, https://aclr.orgfiNeekly-dlgests/2018/rray'theres-just-something-about-them-predicting-response--to-car-t-cell-therapy.
Piekarz, R.L. et al., "Epigenetic Modifiers: Basic Understanding and Clinical Development" Clinical Cancer Research (2009) vol. 15, No. 12, pp. 3918-3926.
Szablewski, V. et al., "An Epigenetic Regulator-Related Score (EpiScore) Predicts Survival in Patients with Diffuse Large B Cell Lymphoma and Identifies Patients Who May Benefit From Epigenetic Therapy" Oncotarget (2018) vol. 9, No. 27, pp. 19079-19099.
Ahmed, Nabil, et al., "HER2-Specific Chimeric Antigen Receiptor-Modified Virus-specific T Cells for Progressive Glioblastoma A Phase 1 Dose-Escalation Trial", JAMA Oncol. 2017:3(8), doi:10.1001/jamaoncol.2017.0184, Apr. 20, 2017, pp. 1094-1101.

(Continued)

*Primary Examiner* — Peter Johansen

(74) *Attorney, Agent, or Firm* — Troutman Pepper Locke LLP

(57) ABSTRACT

The application provides T cell gene expression signatures that can be used to predict T cell therapy outcomes.

17 Claims, 34 Drawing Sheets

Specification includes a Sequence Listing.

(56) References Cited

OTHER PUBLICATIONS

Biburger, Marcus, et al., "A Novel Bispecific Tetravalent Antibody Fusion Protein to Target Costimulatory Activity for T-cell Activation to Tumor Cells Overexpressing ErbB2/HER2" J. Mol. Biol (2005) 346, doi:10.1016/j.jmb.2004.12.052, pp. 1299-1311.
Youngblood, Ben, et al., "Effector CD8 T cells dedifferentitate into long-lived memory cells" vol. 000, Nature, 2017, doi:10.1038/nature25144, pp. 1-17.
Abdelsamed, Hossam A., et al., "Human memory DC8 T cell effector potential is epigenetically preserved during in vivo homeostatis" The Rockefeller University Press, J. Exp. Med., 2017, vol. 214, No. 6, https://doi.org/10.1084/jem.20161760, pp. 1593-1606.
Communication (International Search Report/Written Opinion) issued by the International Searching Authority in International Application No. PCT/US20/27280 dated Jul. 24, 2020, 5 pages total.
Fraietta, Joseph A., et al. "Determinants of response and resistance to CD19 chimeric antigen receptor (CAR) T cell therapy of chronic lymphocytic leukemia", Nat Med. May 2018; 24(5): doi: 10.1038/s41591-018-0010-1; pp. 563-571.
USPTO, Non-Final Office Action Dated Jan. 8, 2025 For Related U.S. Appl. No. 17/602,524.
Venugopal et al., "DNMT3A Harboring Leukemia-Associated Mutations Directs Sensitivity to DNA Damage at Replication Forks," Clin. Cancer Res. Oct. 28, 2021; 28 (4): 756-69.
Herek et al., "DNMT3A mutations define a unique biological and prognostic subgroup associated with cytotoxic T cells in PTCL-NOS," Blood. Sep. 15, 2022; 140 (11): 1278-90.
Yang et al., "DNMT3A in haematological malignancies," Nat. Rev. Cancer. Mar. 2015; 15 (3): 152-65.
Johnston et al., "Tyrosine phosphorylation and activation of STAT5, STAT3, and Janus kinases by interleukins 2 and 15," Proc. Natl. Acad. Sci. USA. Sep. 12, 1995; 92 (19):8705-9.
Shum et al., "Constitutive Signaling from an Engineered IL7 Receptor Promotes Durable Tumor Elimination by Tumor-Redirected T Cells," Cancer Discov. Nov. 2017; 7 (11): 1238-1247.
Zhang et al., "Structural basis for DNMT3A-mediated de novo DNA methylation," Nature. Feb. 15, 2018; 554 (7692):387-91.
Xu et al., "DNMT3A Arg882 mutation drives chronic myelomonocytic leukemia through gene expression/DNA methylation in hematopoietic cells," Proc. Natl. Acad. Sci. USA. Feb. 18, 2014; 111 (7): 2620-5.
Zhou et al., "Activation of JAK2/STAT5 Pathway Reduces Expression Level of DNMT3a in MPN Cell Line," Blood. 2019; 134 (Supp. 1): 5394; pp. 1-2.
Fried et al., "Frequency, onset and clinical impact of somatic DNMT3A mutations in therapy-related and secondary acute myeloid leukemia," Haematologica. Feb. 2012; 97 (2): 246-50.
Chen et al., "Cancer cell-intrinsic PD-1: Its role in malignant progression and immunotherapy," Biomed. Pharmacother. Nov. 2023; 167: 115514; pp. 1-10.
Feng et al., "Hematopoietic-specific heterozygous loss of Dnmt3a exacerbates colitis-associated colon cancer," J. Exp. Med. Nov. 6, 2023; 220 (11): e20230011; pp. 1-19.
Andrews et al., "Reconstitution of a Functional Human Type II IL-4/IL-13 Receptor in Mouse B Cells: Demonstration of Species Specificity," J. Immunol. Feb. 1, 2001; 166 (3): 1716-22.
Wing et al., "Characterization of human CD25 CD4 T cells in thymus, cord and adlut blood," Immunology. Jun. 2002; 106 (2): 190-9.
Wu et al., "PD-L1 Distribution and Perspective for Cancer Immunotherapy—Blockade, Knockdown, or Inhibition," Front. Immunol. Aug. 27, 2019; 10: 2022; pp. 1-15.
Hennighausen, L. and Robinson, G.W., "Interpretation of cytokine signaling through the transcription factors STAT5A and STAT5B", Genes & Dev (2008) vol. 22(6), pp. 711-721.
Themeli et al. "Generation of tumor-targeted human T lymphocytes from induced pluripotent stem cells for cancer therapy", Nat Biotechnol. (2013) vol. 10, pp. 928-933.
Communication (Written Opinion) issued by the International Searching Authority in International Application No. PCT/US20/27280 dated Jul. 24, 2020, 10 pages total.

* cited by examiner

T CELL GENE EXPRESSION ANALYSIS FOR USE IN T CELL THERAPIES

CROSS-REFERENCE TO RELATED APPLICATIONS

This application is a National Stage Entry of International Application No. PCT/US2020/027291, filed Apr. 8, 2020 which claims priority to U.S. Provisional Application Nos. 62/842,260, filed May 2, 2019, all of which are herein incorporated by reference in its entireties.

STATEMENT REGARDING FEDERALLY SPONSORED RESEARCH

This invention was made with government support under grant number AI114442 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 2, 2020, is named 243734_000132_SL.txt and is 763 bytes in size.

FIELD

The application relates to T cell gene expression signatures that can be used to predict T cell therapy outcomes.

BACKGROUND

Cellular immunotherapy with adoptively transferred chimeric antigen receptor (CAR) modified T cells is an attractive approach to improve the outcomes for patients with cancer. However, even for the most successful CAR T cell therapy, CD19-CAR T cell therapy for CD19+ acute lymphoblastic leukemia (ALL), only 50% of patients have responses that last more than one year (Maude et al., NEJM 2018). Complete responses are much lower for CD19+ chronic lymphatic leukemia (Fraietta et al., Nature Med 2018), and only few long term survivors have been reported for CAR T cell therapies targeting solid tumor antigens such as HER2 (Ahmed et al., JCO 2015). Thus, there is a great need in the art to develop methods for predicting individual patient's responsiveness to CAR T cell therapies prior to the use of such therapies, so that an appropriate individual treatment plan can be developed.

The need to develop predictive markers does not only apply to CAR T cell therapies, but also to all forms of T cell therapies, which include therapies with i) T cells that express an endogenous αβ TCR, which is specific for a peptide derived from viral or tumor-associated antigens (including neoantigens); ii) T cells that transgenically express an αβ TCR, which is specific for a peptide derived from viral or tumor-associated antigens (including neoantigens); iii) T cells that transgenically express bispecific antibodies, which recognize viral or tumor-associated antigens (including neoantigens)/or a peptide derived from them and an activating molecule expressed on T cells such as CD3; and/or iv) T cells that are generated via stimulation with for examples but not limited to peptides, antigen presenting and/or artificial antigen presenting cells (in vitro sensitized [IVS] T cell therapy). Lastly, T cell therapies in which the therapeutic genes are delivered in vivo are included (in vivo T cell therapy).

SUMMARY OF THE INVENTION

As specified in the Background section above, there is a great need in the art for developing methods for predicting individual patient's responsiveness to CAR T cell therapies and other T cell therapies prior to the use of such therapies. The present application addresses these and other needs.

In one aspect provided herein is a method for predicting a subject's responsiveness to an autologous T cell therapy. The method comprises: a) determining gene expression level of one or more genes in a T cell sample isolated from the subject, wherein one or more of said genes are methylation targets of DNA (cytosine-5)-methyltransferase 3A (DNMT3A), b) generating a Diagnostic Expression Score for the T cell sample isolated from the subject by calculating and summing absolute or weighted gene expression level(s) determined in step (a), or by calculating and summing relative gene expression level(s) relative to reference expression level(s) obtained using responders and non-responders in a reference dataset, and c) (i) determining that the subject is not likely to respond to an autologous T cell therapy if the Diagnostic Expression Score generated in step (b) is less than a threshold score; (ii) determining that the subject is likely to respond to an autologous T cell therapy if the Diagnostic Expression Score generated in step (b) is greater than the threshold score. In some embodiments, the Diagnostic Expression Score is generated by Z-score summation and the threshold score is 0.

In some embodiments, the subject has a cancer, an infectious disease, an inflammatory disorder, or an autoimmune disease.

In some embodiments, the method further comprises improving the subject's T cell functioning in T cell therapies. In some embodiments, improving the subject's T cell functioning in T cell therapies comprises inhibiting DNMT3A-mediated de novo DNA methylation and/or activating STAT5 signaling pathway in the subject's T cells.

In some embodiments, inhibiting DNMT3A-mediated de novo DNA methylation in the subject's T cells is achieved by inhibiting enzymatic activity of DNMT3A protein or making DNMT3A gene deleted or defective. In some embodiments, the enzymatic activity of the DNMT3A protein is inhibited by exposing the cell to a DNMT3A active site inhibitor. In some embodiments, the DNMT3A gene is mutated in DNMT3A catalytic domain so that the enzymatic activity of the DNMT3A protein is inhibited. In some embodiments, the level of functional DNMT3A protein in the cell is decreased by 50% or more.

In some embodiments, the STAT5 signaling pathway is activated by either stimulating the T cell with a signaling molecule or genetically modifying the T cell to express a signaling molecule. In some embodiments, the signaling molecule is a common gamma chain cytokine. In some embodiments, the cytokine is IL-15, IL-7, IL-2, IL-4, IL-9, or IL-21. In some embodiments, the STAT5 signaling pathway is activated by modifying the T cell to express a constitutively active cytokine receptor or a switch receptor. In some embodiments, the constitutively active cytokine receptor is a constitutively active IL7 receptor (C7R). In some embodiments, the switch receptor is an IL-4/IL-7 receptor or an IL-4/IL-2 receptor.

In various embodiments, improving the subject's T cell functioning as described herein is conducted ex vivo or in vitro.

In some embodiments, the method further comprises repeating the method described to predict a subject's responsiveness to an autologous T cell therapy on the subject's T cells which were treated to improve the subject's T cell functioning.

In some embodiments, if the subject is determined in step (c) as not likely to respond to an autologous T cell therapy, the method further comprises administering to the subject an alternative therapy which is not a T cell therapy. The alternative therapy may be selected from antiviral therapies, bone marrow transplant, chemotherapies, checkpoint blockade, and any combinations thereof.

In some embodiments, the subject is determined in step (c) as likely to respond to an autologous T cell therapy, the method further comprises using the subject's T cells for an autologous T cell therapy.

In another aspect provided herein is a method for determining if T cells of a subject can be used for an allogeneic T cell therapy. The method comprises a) determining gene expression level of one or more genes in a T cell sample isolated from the subject, wherein one or more of said genes are methylation targets of DNA (cytosine-5)-methyltransferase 3A (DNMT3A), b) generating a Diagnostic Expression Score for the T cell sample isolated from the subject by calculating and summing absolute or weighted gene expression level(s) determined in step (a), or by calculating and summing relative gene expression level(s) relative to reference expression level(s) obtained using responders and non-responders in a reference dataset, and c) (i) determining that the T cells of the subject cannot be used for an allogeneic T cell therapy if the Diagnostic Expression Score generated in step (b) is less than a threshold score; (ii) determining that the T cells of the subject can be used for an allogeneic T cell therapy if the Diagnostic Expression Score generated in step (b) is greater than the threshold score. In some embodiments, the Diagnostic Expression Score is generated by Z-score summation and the threshold score is 0.

In some embodiments, the method further comprises improving the subject's T cell functioning in T cell therapies. In some embodiments, improving the subject's T cell functioning in T cell therapies comprises inhibiting DNMT3A-mediated de novo DNA methylation and/or activating STAT5 signaling pathway in the subject's T cells.

In some embodiments, inhibiting DNMT3A-mediated de novo DNA methylation in the subject's T cells is achieved by inhibiting enzymatic activity of DNMT3A protein or making DNMT3A gene deleted or defective. In some embodiments, the enzymatic activity of the DNMT3A protein is inhibited by exposing the cell to a DNMT3A active site inhibitor. In some embodiments, the DNMT3A gene is mutated in DNMT3A catalytic domain so that the enzymatic activity of the DNMT3A protein is inhibited. In some embodiments, the level of functional DNMT3A protein in the cell is decreased by 50% or more.

In some embodiments, the STAT5 signaling pathway is activated by either stimulating the T cell with a signaling molecule or genetically modifying the T cell to express a signaling molecule. In some embodiments, the signaling molecule is a common gamma chain cytokine. In some embodiments, the cytokine is IL-15, IL-7, IL-2, IL-4, IL-9, or IL-21. In some embodiments, the STAT5 signaling pathway is activated by modifying the T cell to express a constitutively active cytokine receptor or a switch receptor. In some embodiments, the constitutively active cytokine receptor is a constitutively active IL7 receptor (C7R). In some embodiments, the switch receptor is an IL-4/IL-7 receptor or an IL-4/IL-2 receptor.

In various embodiments, improving the subject's T cell functioning as described herein is conducted in vitro.

In some embodiments, the method further comprises repeating the method described to determine if T cells can be used for an allogeneic T cell therapy on the subject's T cells which were treated to improve the subject's T cell functioning.

In some embodiments, if it is determined in step (c) that the T cells of the subject can be used for an allogeneic T cell therapy, the method further comprises using the subject's T cells for an allogeneic T cell therapy.

In various embodiments, methods described herein comprise obtaining a sample of T cells from the subject prior to step (a). In some embodiments, the sample of T cells is derived from blood, marrow, or tissue of the subject. In some embodiments, the subject has cancer and the sample of T cells is derived from a tumor of the subject.

In various embodiments, methods described herein comprise stimulating the T cells in vitro or ex vivo prior to step (a). In some embodiments, the T cells are stimulated using anti-CD3 and anti-CD28 stimulation.

In various embodiments, determining the gene expression level in step (a) comprises isolating mRNA from the T cells. In some embodiments, determining the gene expression level in step (a) is performed using mRNA sequencing, microarray gene expression profiling, or qPCR.

In various embodiments, methods described herein further comprise banking the subject's T cells.

In various embodiments, the DNMT3A target gene(s) is selected from the genes recited in Table 1.

In various embodiments, the DNMT3A target gene(s) is selected from the genes recited in Table 2.

In various embodiments, the DNMT3A target gene(s) is selected from the genes recited in Table 3.

In various embodiments, methods described herein comprise determining the expression level of 10 or more DNMT3A target genes in step (a). In some embodiments, the method comprises determining the expression level of RORA, EOMES, STAT1, EGR2, ASCL1, BACH2, E2F5, ZBTB16, IRF4, HIC1, BCL3, CBFA2T3, TRPS1, NFKBIA, EGR3, KLF7, TCF7, NR4A3, SETBP1, EGR1, MYB, TFAP2A, BCL6, LEF1, and NRIP1 genes in step (a).

In various embodiments, the T cell is selected from a CD8+ T cell, a CD4+ T cell, a cytotoxic T cell, an αβ T cell receptor (TCR) T cell, a natural killer T (NKT) cell, a γδ T cell, a memory T cell, a T-helper cell, and a regulatory T cell (Treg).

In various embodiments, the subject is human.

In various embodiments, the T cell therapy is a CAR T cell therapy. In various embodiments, the T cell therapy is an αβ TCR therapy. In various embodiments, the T cell therapy is a γδ TCR therapy. In various embodiments, the T cell therapy is an iNKT therapy. In various embodiments, the T cell therapy is a tumor-infiltrating lymphocyte (TIL) therapy. In various embodiments, the T cell therapy is an in vitro sensitized (IVS) T cell therapy. In various embodiments, the T cell therapy is an in vivo T cell therapy.

These and other aspects of the present invention will be apparent to those of ordinary skill in the art in the following description, claims and drawings.

DETAILED DESCRIPTION

Figure 1:
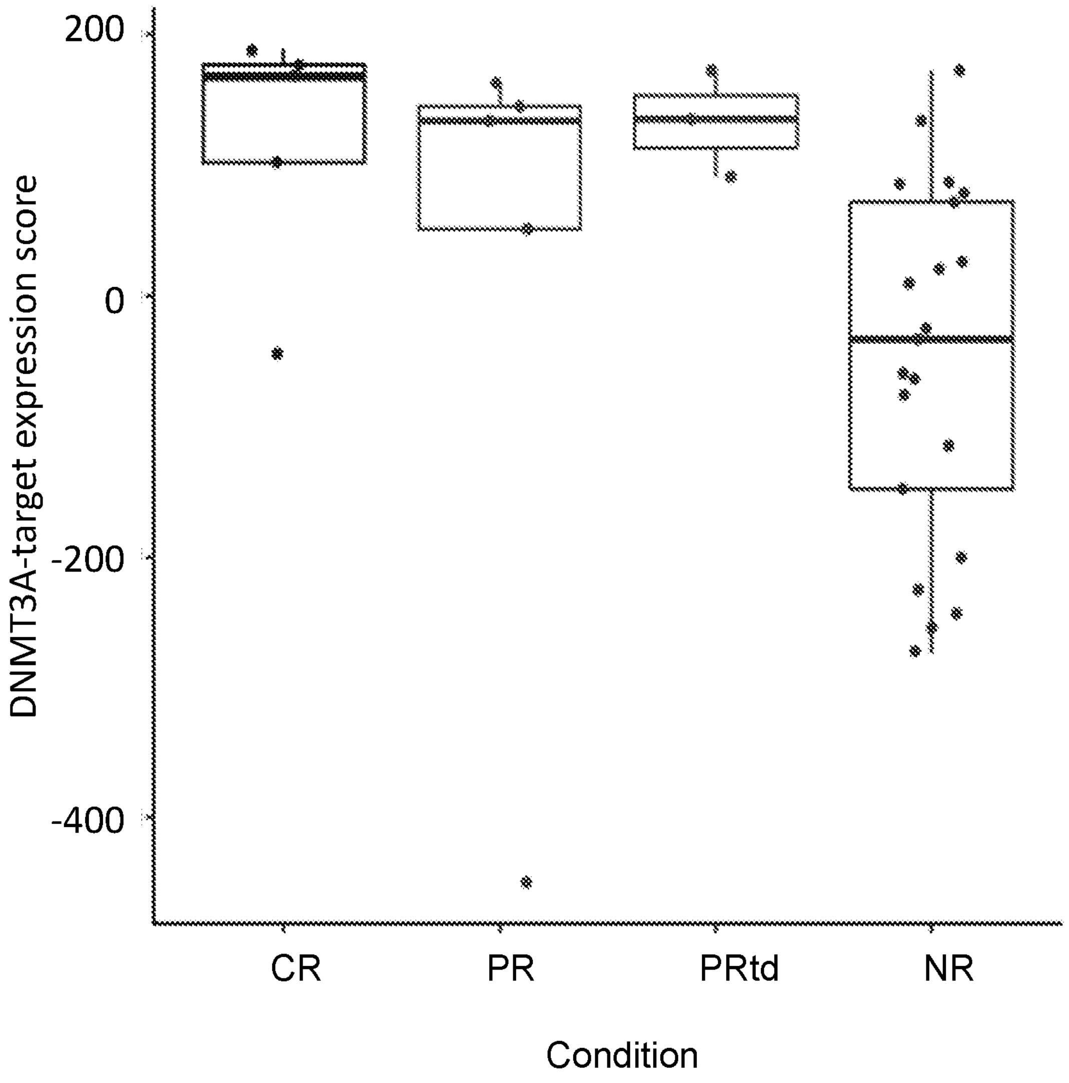
FIG. 1 is a plot showing the comparison of the expression score of DNMT3A target genes in the CAR T-cell products prior to infusion between patients with a Complete Response (CR), Partial Response (PR), Partial Response with Relapse (PRtd), and No Response (NR).

The present invention is based on an unexpected discovery that relatively higher levels of expression of certain genes such as genes which are methylation targets of DNA (cytosine-5)-methyltransferase 3A (DNMT3A) in a patient's T-cell products correlate with increased likelihood of such patient's responsiveness to T cell therapies. In some embodiments, the T cell gene expression signature comprises one or more genes which are methylation targets of DNMT3A. In one specific embodiment, such target genes of DNMT3A are selected from the genes provided in Table 1. In another specific embodiment, such target genes of DNMT3A are selected from the genes provided in Table 2. In yet another specific embodiment, such target genes of DNMT3A are selected from the genes provided in Table 3. In some embodiments, the T cell gene expression signature comprises at least 10 genes. In one specific embodiment, the T cell gene expression signature comprises the 25 genes listed in Table 3: namely RORA, EOMES, STAT1, EGR2, ASCL1, BACH2, E2F5, ZBTB16, IRF4, HIC1, BCL3, CBFA2T3, TRPS1, NFKBIA, EGR3, KLF7, TCF7, NR4A3, SETBP1, EGR1, MYB, TFAP2A, BCL6, LEF1, and NRIP1.

The gene expression signatures of the present invention may be useful for, for example but not limited to, (1) predicting individual patient's responsiveness to an autologous CAR T cell therapy prior to initiation of such therapy; (2) determining if a given subject can be used as a T cell donor for allogeneic CAR T cell therapies (e.g., HaploCAR T cell therapy, using T cells obtained from a close relative [e.g., parents, siblings]; universal CAR T cell therapy, using T cells from a donor unrelated to the patient also known as "off-the-shelf" CAR T cell therapy); (3) determining if patient's or donor's T cells should be subject to additional treatment(s) to improve their functioning in CAR T cell therapies (such as but not limited to, inhibition of DNMT3A-mediated de novo DNA methylation [e.g., by inhibiting enzymatic activity of DNMT3A protein or making DNMT3A gene deleted or defective] and/or activation of STAT5 signaling pathway in the T cells); (4) determining if a CAR T cell therapy should be combined with other therapeutic agents or therapies (such as but not limited to, checkpoint blockade, enhanced expression of genes such as IL15, antiviral therapies, bone marrow transplant, chemotherapies, and any combinations thereof).

In certain embodiments, methods of the present invention include obtaining T cells and testing for potential utility in CAR T cell therapy before beginning any other therapies. The T cells may be banked even if they are not planned for use in CAR T cell therapy immediately.

While the DNMT3A score has been developed to predict efficacy of CAR T cells, it can be applicable to all other forms of T cell therapy in which T cells are obtained from a donor and manipulated for therapeutic intent ex vivo. It is applicable, since DNMT3A regulates transcriptional programs that prevent exhaustion in all T cells (Youngblood et al., Nature 2017; Abdelsamed et al., JEM 2017; Ghoneim et al., Cell 2017; each of which is hereby incorporated by reference in its entirety) and not only CAR T cells. Thus the score can be applicable to, for example but not limited to, cell therapies with conventional or genetically-modified $\alpha\beta$ TCR T cells, $\gamma\delta$ T cells, iNKT cells, or tumor infiltrating lymphocytes (TILs).

In some embodiments, the methods of the present disclosure may be carried out using one or more steps from the process described below.

(a) Obtaining T Cells

A sample of the T cells being proposed for use in T cell product generation may be obtained from a subject. This could be obtained from peripheral blood (e.g. standard blood draw, leukapheresis, sorting of antigen-specific T cells [e.g. tetramer, pentamer, or streptamer sorting, IFN$\zeta$ capture assay]) or a tumor biopsy (e.g. tumor infiltrating lymphocytes [TIL]). In addition, T cells could be generated from induced pluripotent stem (IPS) cells. T cells may be isolated using standard procedures that match those for T cell product preparation. T cells could also be obtained during T cell product generation. Unstimulated T cells could be used for mRNA extraction (see step (c)) or simulated prior to mRNA extraction as described in step (b).

(b) Stimulation of T Cells

T cells may be stimulated ex vivo or in vitro using standard procedures known in the art, such as, e.g., anti-CD3 and anti-CD28 stimulation (e.g., using Gibco™ Dynabeads™ Human T-Activator CD3/CD28), PMA/Ionomycin stimulation, or stimulation with polyclonal stimulators such as Concanavalin A with or without cytokines such as IL2, IL7, and/or IL15. In addition, antigen presenting cells (APCs) such as dendritic cells or monocytes, or artificial APCs such as K562, genetically-modified to express HLA molecules, antigens, or immune stimulatory molecules may be used for T cell stimulation. Further, tumor cells or subcellular fractions of cells such as exomes may be used for T cell stimulation. As needed T cells may be expanded by adding additional cytokines such as IL2, IL7, and/or IL15 and/or repeating the entire stimulation procedure.

(c) mRNA Extraction mRNA may be extracted from the stimulated T cells for gene expression analysis. Methods of extraction of RNA are well known in the art and are described, for example, in Sambrook J., et al., "Molecular Cloning: A Laboratory Manual", Second Ed. (Coldspring Harbor Laboratory Press, Cold Spring Harbor, N.Y., 1989, Volume 1, Chapter 7), which is incorporated herein by reference in its entirety.

(d) Gene Expression Analysis

Extracted mRNA may be subjected to gene expression analysis. Non-limiting examples of techniques that can be used for gene expression analysis include mRNA sequencing, microarray gene expression profiling, and qPCR.

(e) Evaluation of Target Genes

The expression of one or more target genes may be analyzed. In some embodiments, the target genes may be selected from the list of DNMT3A target genes provided in Table 1, Table 2 or Table 3.

In some embodiments, the T cell gene expression signature comprises at least about 10, about 15, about 20, about 25, about 30, about 35, about 40, about 45, about 50, about 55, about 60, about 65, about 70, about 75, about 80, about 85, about 90, about 95, about 100, about 110, about 115, about 120, about 125, about 130, about 140, about 150, about 160, about 170, about 180, about 190, or about 200 genes selected from the genes provided in Table 1. In some embodiments, the T cell gene expression signature comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 115, 120, 125, 130, 135, 140, 145, 150, 160, 170, 180, 190, 200 or more genes selected from the genes provided in Table 1.

In some embodiments, the T cell gene expression signature comprises at least about 10, about 15, about 20, about 25, about 30, about 35, about 40, about 45, about 50, about 55, about 60, about 65, about 70, about 75, about 80, about 85, about 90, about 95, or about 100 genes selected from the genes provided in Table 2. In some embodiments, the T cell gene expression signature comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, or 107 genes selected from the genes provided in Table 2.

In some embodiments, the T cell gene expression signature comprises 10, 11, 12, 13, 14, 15, 16, 17, 18, 19, 20, 21, 22, 23, 24, or 25 genes selected from the genes provided in Table 3.

(f) Generation of Expression Score

Expression levels of the target genes may be compared to known responders and non-responders in a reference dataset to generate an Expression Score. The "Expression Score" can refer to a summation of absolute, weighted, or relative gene expression values that is calculated and interpreted relative to the reference dataset. For example, the reference dataset may comprise known responders and non-responders from publicly available expression data (e.g., Fraietta et al., Nature Medicine 2018 May; 24(5):563-57, which is incorporated herein by reference in its entirety); this reference dataset may be expanded to include data from additional trials or may be changed entirely to provide disease-specific points of comparison or to further refine the predictive value of the Expression Score. Using one or more of the target genes, a set of Reference Expression Scores can be generated from the reference dataset, for example by summing the Z-scores of the expression of those genes, which provides a range of scores that overlaps known responders and known non-responders. A Diagnostic Expression Score can then be generated for a sample of interest by calculating and summing absolute or weighted gene expression values for comparison to the Reference Expression Scores, or by calculating and summing relative gene expression values relative to the variation in expression observed within the reference dataset. This process thereby provides a diagnostic score based on known patterns of diagnostic outcomes with regard to specific genes (which are identified herein) underlying the mechanisms associated with those outcomes.

(g) Data Interpretation

The expression score may be interpreted in relative terms: e.g., higher is better, lower is worse. Higher means overall more expression of genes (for expression scores based on Z-score summations specifically, higher than average across the reference dataset) whereas lower means overall lower expression of genes (for expression scores based on Z-score summations specifically, lower than average across the reference dataset).

Thresholds for clinical recommendations can be created. One exemplary set of thresholds for Z-score based summations may be: i) expression score less than zero indicates low chance of clinical response; and ii) expression score greater than zero indicates high chance of clinical response or poised T cells. In this example, when the score equals zero it indicates that the cumulative expression of the genes is "average" among the reference dataset. In the case that the expression score is based on absolute or weighted summations of expression values, the threshold can be set based on the observed delineations between known responders and non-responders. It is to be understood that the thresholds may be adjusted as additional comparison data become available.

(h) Clinical Recommendations

General and/or specific clinical recommendations can be made based on the patient's expression score relative to the thresholds outlined above in the context of other patient-specific information. Some of these clinical suggestions may be predictive of a time in the future when T cell therapy is integrated to standard clinical practice as opposed to a last resort.

When a low chance of clinical response is indicated (e.g., by a relative diagnostic expression score less than zero): (1) If the patient has not previously received other therapies, T cells may be banked but alternative therapies before T cell therapy should be attempted. New T cell samples may be obtained and banked intermittently to re-assess for any changes. The complete or partial effectiveness of alternative therapies may make room for the return of appropriately poised T cells, which can be assessed and banked in the event of a future relapse (e.g., antiviral therapies, bone marrow transplant, or chemotherapy may allow for T cell recuperation). (2) If the patient has experienced repeated failures of alternative therapies, alternative approaches should be considered which include but are not limited to: i) T cell therapy with additional genomic engineering (e.g., DNMT3A knockout, transgenic expression of IL15, or other known or as-of-yet unknown alterations that can increase long-lived effector potential of engineered T cells); ii) combination therapy (e.g., T cell therapy with the addition of checkpoint blockade); iii) HaploCAR therapy, using expression-score tested T cells obtained from a close relative (e.g., parent, sibling); and iv) "off-the-shelf" CAR T cell therapy (e.g., using T cells from a donor unrelated to the patient).

When a high chance of clinical response is indicated (e.g., by a relative diagnostic expression score greater than zero): (1) T cells may be banked for future production of the therapeutic T cell product even if T cell therapy is not considered as initial therapy, because alternative therapies may impact the potential utility of the patient's T cells in the future when the generation of a therapeutic T cell therapy may become necessary; (2) Use of these T cells for T cell therapy can be considered in place of other therapies (e.g., chemotherapies, antiviral therapies) in order to reduce treatment-based side effects.

In additional embodiments, methods of the present invention involve determining the methylation status at the promoter of the target genes. Promoter methylation may be indicative of the gene expression levels.

Definitions

The term "immune effector cell" as used herein refers to a cell that is involved in an immune response, e.g., in the promotion of an immune effector response. Non-limiting examples of immune effector cells include T cells (e.g., αβ T cells and γδ T cells), B cells, natural killer (NK) cells, natural killer T (NKT) cells, mast cells, and myeloid-derived phagocytes. Stem cells, such induced pluripotent stem cells (iPSCs), that are capable of differentiating into immune cells are also included here.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a CD8+ T cell, a CD4+ T cell, a helper T cell or T-helper cell (HTL; CD4+ T cell), a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "αβ T cell receptor (TCR) T cells", which refer to a population of T cells that possess a TCR composed of α- and β-TCR chains. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs", which refer to T cells that suppress an abnormal or excessive immune response and play a role in immune tolerance. Tregs cells are typically transcription factor Foxp3-positive CD4+ T cells and can also include transcription factor Foxp3-negative regulatory T cells that are IL-10-producing CD4+ T cells.

The terms "natural killer cell" and "NK cell" are used interchangeable and used synonymously herein. As used herein, NK cell refers to a differentiated lymphocyte with a CD16+CD56+ and/or CD57+ TCR-phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

The term "signaling molecule" as used herein, refers to any molecule that is capable of inducing a direct or indirect response in at least one cellular signaling pathway. The response may be stimulatory or inhibitory. One of the cellular signaling pathways may be the STAT5 signaling pathway.

The term "switch receptor" used herein refers to a receptor that is capable of converting a potentially inhibitory signal into a positive signal. Switch receptors are also known as inverted cytokine receptors.

The term "chimeric antigen receptor" or "CAR" as used herein is defined as a cell-surface receptor comprising an extracellular target-binding domain, a transmembrane domain and a cytoplasmic domain, comprising a lymphocyte activation domain and optionally at least one co-stimulatory signaling domain, all in a combination that is not naturally found together on a single protein. This particularly includes receptors wherein the extracellular domain and the cytoplasmic domain are not naturally found together on a single receptor protein. The chimeric antigen receptors of the present invention are intended primarily for use with lymphocyte such as T cells and natural killer (NK) cells.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The term "antigen-binding moiety" refers to a target-specific binding element that may be any ligand that binds to the antigen of interest or a polypeptide or fragment thereof, wherein the ligand is either naturally derived or synthetic. Examples of antigen-binding moieties include, but are not limited to, antibodies; polypeptides derived from antibodies, such as, for example, single chain variable fragments (scFv), Fab, Fab', F(ab')2, and Fv fragments; polypeptides derived from T Cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

The terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910, each of which are incorporated by reference in their entirety for all purposes. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass. Also included are "bispecific antibodies", which refer to antibodies that are capable of binding to two different antigens or different epitopes of the same antigen.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLOPACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

Host cells of the present invention include T cells and natural killer cells that contain the DNA or RNA sequences encoding the CAR and express the CAR on the cell surface. Host cells may be used for enhancing T cell activity, natural killer cell activity, treatment of cancer, and treatment of autoimmune disease.

The terms "activation" or "stimulation" means to induce a change in their biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The terms "genetically modified" or "genetically engineered" refers to the addition of extra genetic material in the form of DNA or RNA into a cell.

As used herein, the term "derivative" in the context of proteins or polypeptides (e.g., CAR constructs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a derivative of; (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a derivative of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a derivative of; (d) a polypeptide encoded by nucleic acids can hybridize under high, moderate or typical stringency hybridization conditions to nucleic acids encoding the polypeptide it is a derivative of; (e) a polypeptide encoded by a nucleotide sequence that can hybridize under high, moderate or typical stringency hybridization conditions to a nucleotide sequence encoding a fragment of the polypeptide, it is a derivative of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a derivative of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin).

Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In some embodiments, the vector is a viral vector such as, but not limited to, viral vector is an adenoviral, adeno-associated, alphaviral, herpes, lentiviral, retroviral, baculoviral, or vaccinia vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in antitumor activity (e.g., cancer cell death killing ability), among others apparent from the understanding in the art and the description herein. In some embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In some embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "inhibit" or "inhibition" as used herein refer to reducing a function or activity to an extent sufficient to achieve a desired biological or physiological effect. Inhibition may be complete or partial.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ Additional techniques are explained, e.g., in U.S. Pat. No. 7,912,698 and U.S. Patent Appl. Pub. Nos. 2011/0202322 and 2011/0307437.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Examples

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Gene Expression signature with complete list of DNMT3A targets

To demonstrate the usefulness of the developed gene expression signature, a publicly available gene expression dataset was analyzed which was collected from CD19-CAR T-cell products that were used in a clinical study of 41 patients with chronic lymphocytic leukemia (CLL). See Fraietta et al., Nature Medicine 2018 May; 24(5):563-57, which is incorporated herein by reference in its entirety. For 34 out of 41 patients gene expression data were available.

The dataset analyzed from the Fraietta et al. publication consists of RNAseq data from stimulated CTL019 infusion products for patients who either exhibited a Complete Response to therapy (CR, n=5), exhibited a Partial Response (PR, n=5), exhibited a Partial Response followed by a relapse that had transformed into aggressive B cell lymphoma (PRtd, n=3), or exhibited No Response (NR, n=21). The median peak expansion (MPE) of CAR T cells in these 4 groups of patients was 58,570 (CR), 13,257 (PR), 130,258 (PRtd), and 205 (NR).

Transcript counts were obtained from Fraietta et al. 2018 "Supplemental Table 5b: Transcriptomic profiling of CAR-stimulated CTL019 infusion products" and filtered, normalized, and analyzed using the R packages 'edgeR' (Robinson M D et al., Bioinformatics. 2010; 26(1):139-40) and 'limma' (Ritchie M E. et al., Nucleic Acids Res. 2015; 43(7):e47).

The target genes identified from DNMT3A-knockout CAR T cells (herein referred to as "DNMT3A targets", listed in Table 1) were assessed. The DNMT3A targets were identified using whole genome DNA methylation profiling. Whole genome DNA methylation profiling was performed using CD8 T cells from two independent wild-type (WT) vs DNMT3A knockout CAR T cell co-culture experiments. During these experiments, CAR T cells were continually re-cultured with fresh tumor cells every week. After the WT T cells became terminally differentiated, whole genome methylation profiling was performed to identify DNMT3A-associated differences in methylation profiles. The two experiments had different receptors, further ensuring that the differentially methylated regions (DMRs) identified were related to T cell biology and not the receptors. From these two datasets DMRs that were exactly shared (the same genomic coordinates) between the two experiments were selected. DMRs were then assigned to the nearest genes. This list of genes was then used for the analyses to assess for an association between responder and non-responder CAR T cell gene expression data. The selection criteria for the list was considered very stringent as only DMRs that were exactly shared among the two experiments were used. 1,033 gene identifiers matched the 1,298 previously identified DNMT3A targets and were used to calculate a relative DNMT3A-target expression score.

A relative DNMT3A-target expression score was calculated, and each gene's log 2-expression was standardized to represent its mean-centered variation in order to equalize the weights of genes that were relatively highly or lowly expressed across the dataset. The expression score was then calculated as the sum of those normalized expression values. In subsequent Examples this score was also calculated using a limited gene set that either included only those differentially expressed genes (DGEs) between in vitro DNMT3A knockout and wildtype cells (as assayed by Affymetrix® Clariom™ S Human microarray; WT N=3, Knockout N=8) or the intersection between these DGEs and the previously identified DNMT3A targets. The nonparametric Kruskal Wallis test and Mann-Whitney U test were used to assess significant variation across the patient outcomes defined by the originating study, and plots were generated with ggplot2 (Wickham H., Springer; 2016).

TABLE 1

| Human DNMT3A target genes |
|---|
| AAK1 |
| ABHD2 |
| ABLIM1 |
| ACOXL |
| ACSF3 |
| ACSL1 |
| ACSL5 |
| ACSL6 |
| ACTB |
| ACTL9 |
| ACTN1 |
| ACTR2 |
| ACVR2A |
| ADAM19 |
| ADAM6 |
| ADAMTS10 |
| ADAP1 |
| ADARB1 |
| ADCY7 |
| ADD3 |
| ADGRE5 |
| ADGRG1 |
| ADORA2A |

TABLE 1-continued

| Human DNMT3A target genes |
|---|
| ADRA2B |
| AEBP2 |
| AGFG1 |
| AGO2 |
| AGPAT3 |
| AGTPBP1 |
| AGTRAP |
| AHNAK |
| AHRR |
| AIM1 |
| AKAP11 |
| AKAP13 |
| AKAP2 |
| AMFR |
| AMZ1 |
| ANAPC1 |
| ANAPC16 |
| ANKRD11 |
| ANKRD33B |
| ANKRD44 |
| ANKRD53 |
| ANXA2P3 |
| ANXA6 |
| ANXA9 |
| AOAH |
| AP1M1 |
| AP1S3 |
| AP2A2 |
| AP2B1 |
| APBA2 |
| APBB1 |
| APBB1IP |
| APH1B |
| APLP2 |
| AQP3 |
| ARFGEF2 |
| ARHGAP10 |
| ARHGAP15 |
| ARHGAP22 |
| ARHGAP31 |
| ARHGEF1 |
| ARHGEF12 |
| ARHGEF18 |
| ARHGEF2 |
| ARID1B |
| ARID3A |
| ARID5A |
| ARID5B |
| ARL3 |
| ARL4C |
| ARRB1 |
| ARX |
| ASAP1 |
| ASCC1 |
| ASCL1 |
| ASIC2 |
| ASPM |
| ASXL1 |
| ATG5 |
| ATM |
| ATP10A |
| ATP1A1 |
| ATP7A |
| ATP8A1 |
| ATP8B1 |
| ATP8B2 |
| ATXN1 |
| ATXN7 |
| AUTS2 |
| B3GNT2 |
| B3GNTL1 |
| B4GALT4 |
| B9D2 |
| BACH2 |
| BAHD1 |
| BANP |
| BATF |
| BATF3 |

TABLE 1-continued

| Human DNMT3A target genes |
|---|
| BBC3 |
| BCAR3 |
| BCAS4 |
| BCAT1 |
| BCKDHB |
| BCL11B |
| BCL2 |
| BCL2L13 |
| BCL2L14 |
| BCL3 |
| BCL6 |
| BCL9 |
| BCL9L |
| BCOR |
| BCR |
| BFSP2 |
| BID |
| BIN1 |
| BIN3 |
| BIRC2 |
| BMPR1A |
| BORCS5 |
| BRD4 |
| BRDTP1 |
| BRF1 |
| BRINP3 |
| BTBD11 |
| BTLA |
| C10orf128 |
| C10orf54 |
| C10orf55 |
| C11orf63 |
| C12orf65 |
| C12orf80 |
| C14orf177 |
| C14orf180 |
| C15orf39 |
| C15orf53 |
| C15orf62 |
| C18orf25 |
| C18orf42 |
| C19orf33 |
| C1orf162 |
| C1QTNF3-AMACR |
| C1QTNF4 |
| C1QTNF6 |
| C20orf27 |
| C2orf48 |
| C3orf17 |
| C3orf18 |
| C4orf22 |
| C4orf47 |
| C7orf72 |
| CA6 |
| CABIN1 |
| CABLES1 |
| CACNA2D3 |
| CAMK2G |
| CAMK4 |
| CAMKK2 |
| CAPZB |
| CARD11 |
| CARNS1 |
| CBFA2T3 |
| CBL |
| CBLB |
| CBLN4 |
| CBX5 |
| CCDC109B |
| CCDC150 |
| CCDC57 |
| CCDC66 |
| CCDC69 |
| CCDC88C |
| CCND2-AS1 |
| CCND3 |
| CCR4 |

TABLE 1-continued

| Human DNMT3A target genes |
|---|
| CCR7 |
| CD101 |
| CD200 |
| CD226 |
| CD244 |
| CD247 |
| CD27 |
| CD28 |
| CD300A |
| CD34 |
| CD47 |
| CD48 |
| CD5 |
| CD6 |
| CD70 |
| CD79A |
| CD8A |
| CD8B |
| CDC45 |
| CDH19 |
| CDH23 |
| CDHR3 |
| CDK17 |
| CDK2AP1 |
| CDKL4 |
| CDKN2A |
| CDKN2A-AS1 |
| CDKN2B |
| CDKN2B-AS1 |
| CEACAM21 |
| CELF1 |
| CELF2 |
| CELP |
| CEP170 |
| CEP41 |
| CEP83 |
| CEP85L |
| CFAP77 |
| CFDP1 |
| CHD7 |
| CHFR |
| CHKA |
| CHMP4B |
| CHMP7 |
| CHST11 |
| CHSY1 |
| CLASP2 |
| CLCN4 |
| CLEC16A |
| CLIC3 |
| CLIC5 |
| CLK1 |
| CMIP |
| CMTM2 |
| CMTM3 |
| CMTM7 |
| CNKSR1 |
| CNTN3 |
| CNTNAP5 |
| COA1 |
| COG1 |
| COL6A3 |
| COLQ |
| COPB1 |
| CORO1C |
| COTL1 |
| COX10 |
| CPPED1 |
| CPXCR1 |
| CRADD |
| CREB1 |
| CREBBP |
| CRIM1 |
| CRLF3 |
| CRTC1 |
| CRTC3 |
| CSGALNACT1 |
| CSK |

TABLE 1-continued

| Human DNMT3A target genes |
|---|
| CSNK1D |
| CSNK1G2 |
| CTAGE1 |
| CTCFL |
| CTDP1 |
| CTDSP2 |
| CTDSPL |
| CTNNA1 |
| CTSZ |
| CUBN |
| CX3CR1 |
| CXCR4 |
| CXCR6 |
| CXXC5 |
| CYFIP2 |
| CYSLTR2 |
| CYTH1 |
| DAB1 |
| DAOA-AS1 |
| DAPK2 |
| DDAH2 |
| DEF6 |
| DENND2D |
| DENND3 |
| DENND5A |
| DGKA |
| DGKD |
| DGKZ |
| DHRS3 |
| DIDO1 |
| DIP2A |
| DIP2B |
| DIS3L2 |
| DLEU1 |
| DMD |
| DMXL1 |
| DNAJB12 |
| DNAJC6 |
| DNMT1 |
| DNMT3A |
| DOC2GP |
| DOCK10 |
| DOCK5 |
| DOCK9 |
| DOK3 |
| DPEP2 |
| DPF3 |
| DPP6 |
| DPYD |
| DTNB |
| DTX2 |
| DUSP14 |
| DYRK1A |
| E2F5 |
| ECE1 |
| EFCAB11 |
| EGR1 |
| EGR2 |
| EGR3 |
| ELK3 |
| ELMO1 |
| ELMSAN1 |
| EMC8 |
| EMX2OS |
| ENPP7P13 |
| EOMES |
| EPB41 |
| EPHB1 |
| EPS15L1 |
| ERGIC1 |
| ERI1 |
| ERI3 |
| ERICH1 |
| ESYT2 |
| ETS1 |
| ETV6 |
| EVL |
| EXOC2 |

TABLE 1-continued

| Human DNMT3A target genes |
|---|
| EXOC4 |
| EYA2 |
| EZH1 |
| EZR |
| F11R |
| FAM102A |
| FAM107B |
| FAM110A |
| FAM134B |
| FAM13A |
| FAM150B |
| FAM178B |
| FAM193A |
| FAM47A |
| FAM53B |
| FAM65B |
| FAM71A |
| FAM72A |
| FAM73A |
| FAM76B |
| FBLN5 |
| FBXL14 |
| FBXW11 |
| FBXW7 |
| FCGBP |
| FCMR |
| FCN3 |
| FDFT1 |
| FES |
| FFAR2 |
| FGD3 |
| FGF17 |
| FGGY |
| FIP1L1 |
| FIRRE |
| FKBP5 |
| FLI1 |
| FLJ21408 |
| FLJ22447 |
| FLJ45079 |
| FLOT1 |
| FNBP1 |
| FOSL2 |
| FOXB1 |
| FOXD2-AS1 |
| FOXK1 |
| FOXN3 |
| FOXO1 |
| FOXO3 |
| FOXP1 |
| FOXP1-AS1 |
| FOXR1 |
| FUNDC2P2 |
| FUT7 |
| FXYD2 |
| FYB |
| FYN |
| G3BP2 |
| GALM |
| GALNT10 |
| GALNT2 |
| GALNT6 |
| GAS7 |
| GATA3 |
| GATAD2A |
| GFOD1 |
| GIMAP4 |
| GIT2 |
| GLB1 |
| GLRX |
| GLTSCR1 |
| GLTSCR1L |
| GNAI3 |
| GNAQ |
| GOLGA5 |
| GPD2 |
| GPR132 |
| GPR55 |

TABLE 1-continued

| Human DNMT3A target genes |
|---|
| GPR65 |
| GRAMD4 |
| GRAP2 |
| GRB2 |
| GRIK3 |
| GRK5 |
| GRK6 |
| GSE1 |
| H3F3C |
| HADH |
| HDAC4 |
| HDAC7 |
| HDGFRP3 |
| HECA |
| HERC1 |
| HERC2P9 |
| HGSNAT |
| HIC1 |
| HIF1A |
| HIPK1 |
| HIPK2 |
| HIVEP2 |
| HIVEP3 |
| HK1 |
| HMGB1 |
| HMGXB4 |
| HOXB-AS3 |
| HOXB3 |
| HPCAL1 |
| HRASLS2 |
| HS3ST4 |
| HSBP1L1 |
| HTRA4 |
| ICA1 |
| ICAM2 |
| ICOS |
| ID2 |
| ID2-AS1 |
| IFFO2 |
| IFITM1 |
| IFITM3 |
| IFITM5 |
| IFNAR2 |
| IFNGR1 |
| IGSF9B |
| IKBKE |
| IKZF1 |
| IKZF3 |
| IL10 |
| IL18RAP |
| IL1RAPL2 |
| IL21R |
| IL2RA |
| IL3 |
| IL31RA |
| IL6 |
| IL6R |
| IL6ST |
| IL7R |
| INF2 |
| INPP5A |
| IQCD |
| IQCE |
| IQGAP2 |
| IQSEC1 |
| IRF4 |
| IRF5 |
| IRX3 |
| ISG20 |
| ISL2 |
| ISM1 |
| ITGA4 |
| ITGA6 |
| ITGAE |
| ITGB1 |
| ITK |
| ITM2B |
| ITM2C |

TABLE 1-continued

| Human DNMT3A target genes |
|---|
| ITPK1 |
| ITPKB |
| ITPKB-IT1 |
| ITPR1 |
| JADE2 |
| JAK1 |
| JAKMIP1 |
| JAML |
| JARID2 |
| JAZF1 |
| JHDM1D-AS1 |
| JMJD6 |
| KANSL1 |
| KAT6B |
| KAT7 |
| KCNC4 |
| KCNIP1 |
| KCNN1 |
| KCNN3 |
| KCNQ4 |
| KDM4B |
| KIAA0319L |
| KIAA0922 |
| KIAA1671 |
| KIAA2012 |
| KIDINS220 |
| KIF24 |
| KIR3DL3 |
| KLF12 |
| KLF13 |
| KLF6 |
| KLF7 |
| KLHDC7B |
| KLHL2 |
| KLHL3 |
| KRTAP12-4 |
| L3MBTL3 |
| LAMA3 |
| LANCL2 |
| LAPTM5 |
| LASPI |
| LBH |
| LBR |
| LCK |
| LCLAT1 |
| LCP2 |
| LDLRAD4 |
| LDLRAP1 |
| LEF1 |
| LEPROTL1 |
| LIG4 |
| LILRA4 |
| LIME1 |
| LIMK2 |
| LINC-PINT |
| LINC00158 |
| LINC00282 |
| LINC00365 |
| LINC00381 |
| LINC00426 |
| LINC00470 |
| LINC00540 |
| LINC00578 |
| LINC00593 |
| LINC00599 |
| LINC00645 |
| LINC00702 |
| LINC00707 |
| LINC00708 |
| LINC00856 |
| LINC00861 |
| LINC00887 |
| LINC00911 |
| LINC00936 |
| LINC00963 |
| LINC00971 |
| LINC01011 |
| LINC01108 |

TABLE 1-continued

| Human DNMT3A target genes |
|---|
| LINC01117 |
| LINC01119 |
| LINC01126 |
| LINC01128 |
| LINC01132 |
| LINC01136 |
| LINC01160 |
| LINC01197 |
| LINC01237 |
| LINC01271 |
| LINC01304 |
| LINC01307 |
| LINC01359 |
| LINC01366 |
| LINC01381 |
| LINC01412 |
| LINC01420 |
| LINC01435 |
| LINC01503 |
| LINC01550 |
| LINC01554 |
| LINC01578 |
| LINC01599 |
| LINC01619 |
| LINC01629 |
| LINS1 |
| LIPC |
| LITAF |
| LMNA |
| LMO7 |
| LMTK2 |
| LOC100129345 |
| LOC100130298 |
| LOC100132735 |
| LOC100288798 |
| LOC100288911 |
| LOC100289473 |
| LOC100505478 |
| LOC100505530 |
| LOC100505658 |
| LOC100506178 |
| LOC100996263 |
| LOC100996286 |
| LOC100996291 |
| LOC101060498 |
| LOC101926941 |
| LOC101927539 |
| LOC101927543 |
| LOC101927630 |
| LOC101927637 |
| LOC101927817 |
| LOC101927851 |
| LOC101927865 |
| LOC101928100 |
| LOC101928794 |
| LOC101929076 |
| LOC101929241 |
| LOC101929331 |
| LOC101929378 |
| LOC101929406 |
| LOC101929452 |
| LOC101929551 |
| LOC101929567 |
| LOC101929698 |
| LOC102546299 |
| LOC102723854 |
| LOC102724511 |
| LOC102724539 |
| LOC102724699 |
| LOC103091866 |
| LOC152225 |
| LOC220729 |
| LOC285847 |
| LOC389033 |
| LOC442497 |
| LPGAT1 |
| LPIN1 |
| LPIN2 |

TABLE 1-continued

| Human DNMT3A target genes |
|---|
| LPP |
| LPP-AS2 |
| LRCH1 |
| LRIG1 |
| LRMP |
| LRRC41 |
| LRRC8C |
| LRRC8D |
| LRRFIP1 |
| LRRK1 |
| LRRN2 |
| LSP1 |
| LTBP3 |
| LTC4S |
| LUZP1 |
| LY86 |
| LY86-AS1 |
| LY9 |
| LYN |
| LZTFL1 |
| LZTS1 |
| LZTS1-AS1 |
| MAB21L3 |
| MACROD2 |
| MAD1L1 |
| MAEA |
| MAF |
| MALT1 |
| MAML2 |
| MAML3 |
| MAN1C1 |
| MANEA-AS1 |
| MAP3K1 |
| MAP3K4 |
| MAP3K7 |
| MAP4K4 |
| MAPK14 |
| MAPKAP1 |
| MAPKBP1 |
| MAPRE1 |
| MAPRE2 |
| MARK2 |
| MATN1 |
| MBOAT1 |
| MBP |
| MBTD1 |
| MBTPS1 |
| MCTP2 |
| MDM4 |
| MDS2 |
| MEAT6 |
| MED12L |
| MED15 |
| MED7 |
| MEF2A |
| MELK |
| METTL7A |
| MEX3C |
| MFHAS1 |
| MFSD2A |
| MGAT4A |
| MGAT5 |
| MGLL |
| MICAL2 |
| MIEN1 |
| MINK1 |
| MIR10A |
| MIR1208 |
| MIR1254-2 |
| MIR133A2 |
| MIR138-2 |
| MIR181A1HG |
| MIR202 |
| MIR24-2 |
| MIR3134 |
| MIR31HG |
| MIR3201 |
| MIR4276 |

TABLE 1-continued

| Human DNMT3A target genes |
| --- |
| MIR4425 |
| MIR4426 |
| MIR4433A |
| MIR4435-2 |
| MIR4435-2HG |
| MIR4471 |
| MIR4487 |
| MIR4492 |
| MIR4493 |
| MIR4494 |
| MIR4632 |
| MIR466 |
| MIR4680 |
| MIR4708 |
| MIR4779 |
| MIR5093 |
| MIR5095 |
| MIR5189 |
| MIR548AN |
| MIR650 |
| MIR6764 |
| MIR6785 |
| MIR8086 |
| MKI67 |
| MKL1 |
| MKLN1 |
| MLANA |
| MLLT3 |
| MLXIP |
| MMP14 |
| MPZL3 |
| MRPS5 |
| MRPS6 |
| MSH3 |
| MSI2 |
| MSL3 |
| MSN |
| MTA1 |
| MTDH |
| MTM1 |
| MTSS1 |
| MUT |
| MVB12B |
| MVP |
| MYB |
| MYEOV |
| MYH9 |
| MYO18A |
| MYO1A |
| MYO3B |
| N4BP2 |
| NAA60 |
| NABP1 |
| NARF |
| NAV2 |
| NBPF8 |
| NCK2 |
| NCOA2 |
| NCOR2 |
| NDFIP1 |
| NDRG1 |
| NEDD9 |
| NEK6 |
| NELL2 |
| NET1 |
| NEURL3 |
| NFATC1 |
| NFATC2 |
| NFKBIA |
| NIN |
| NLK |
| NLRC5 |
| NME4 |
| NMRK1 |
| NMT1 |
| NOL4L |
| NOMO2 |
| NOSIP |

TABLE 1-continued

| Human DNMT3A target genes |
| --- |
| NOTCH 1 |
| NR4A2 |
| NR4A3 |
| NRIP1 |
| NRP1 |
| NSL1 |
| NSMCE1 |
| NT5E |
| NTPCR |
| NUAK2 |
| NUCB2 |
| NUMA1 |
| NUP210 |
| NXPH1 |
| NXPH4 |
| OAT |
| OLIG2 |
| OR4N3P |
| OR5B21 |
| OSR2 |
| OXNAD1 |
| PACSIN2 |
| PAG1 |
| PALD1 |
| PALLD |
| PAPD7 |
| PAQR8 |
| PARP11 |
| PARVB |
| PASK |
| PATZ1 |
| PCAT29 |
| PCBP1-AS1 |
| PCCA |
| PCDHGB3 |
| PCNX |
| PDCD6IP |
| PDE4A |
| PDE7B |
| PDE9A |
| PDIA5 |
| PDK1 |
| PDPK1 |
| PDXK |
| PEBP4 |
| PFKFB2 |
| PFKFB4 |
| PGLYRP2 |
| PGS1 |
| PHF19 |
| PHLDA1 |
| PIAS1 |
| PIGV |
| PIK3C2B |
| PIK3CD |
| PIK3CG |
| PIK3IP1 |
| PIK3R5 |
| PIM3 |
| PIP4K2A |
| PITPNC1 |
| PLAC8 |
| PLCG1 |
| PLCL1 |
| PLCL2 |
| PLEKHA2 |
| PLEKHO1 |
| PLOD2 |
| PLXNA4 |
| PLXNB2 |
| PNRC1 |
| POLR2E |
| POM121 |
| PPCDC |
| PPP1R16B |
| PPP1R37 |
| PPP2R5C |
| PQLC1 |

TABLE 1-continued

| Human DNMT3A target genes |
|---|
| PRDM1 |
| PRDM11 |
| PRDM13 |
| PRDM8 |
| PREP |
| PREX1 |
| PRKAR1B |
| PRKCA |
| PRKCB |
| PRKCH |
| PRKCI |
| PRKCQ |
| PRMT2 |
| PROSER3 |
| PRR3 |
| PRR34 |
| PRR5 |
| PRR7-AS1 |
| PRRC2B |
| PRRX2 |
| PRTFDC1 |
| PSMG1 |
| PTCD3 |
| PTEN |
| PTGER4 |
| PTK2B |
| PTPN18 |
| PTPN6 |
| PTPRC |
| PTPRJ |
| PTPRK |
| PTTG1IP |
| PUDP |
| PUM3 |
| PVRL3 |
| PVT1 |
| PWP2 |
| PXN |
| PYGB |
| R3HDM1 |
| RAB11FIP4 |
| RAB28 |
| RAB37 |
| RAB8B |
| RAD51B |
| RAI1 |
| RALGDS |
| RALGPS1 |
| RAMP1 |
| RANBP3 |
| RAPGEF1 |
| RAPGEF6 |
| RARA-AS1 |
| RARG |
| RASA3 |
| RASGRF2 |
| RASGRP2 |
| RASGRP3 |
| RASSF3 |
| RB1 |
| RBM33 |
| RBM38 |
| RBMS1 |
| RBPJ |
| RCAN3 |
| RCSD1 |
| RDH10-AS1 |
| REC8 |
| REEP3 |
| RERE |
| REV1 |
| RFC2 |
| RFC3 |
| RFFL |
| RGCC |
| RGPD3 |
| RGS1 |
| RGS10 |

TABLE 1-continued

| Human DNMT3A target genes |
|---|
| RGS3 |
| RGS6 |
| RHBDF2 |
| RHOH |
| RHOT1 |
| RILPL1 |
| RIN1 |
| RIN3 |
| RMI2 |
| RNF157 |
| RNF216 |
| RNF4 |
| RNF44 |
| RORA |
| RPL34 |
| RPL34-AS1 |
| RPS6KA1 |
| RPS9 |
| RPTOR |
| RREB1 |
| RRN3P2 |
| RSBN1L |
| RSPH9 |
| RTN4 |
| RTN4RL1 |
| RUNX1 |
| RUNX2 |
| RUNX3 |
| S1PR1 |
| SAE1 |
| SALRNA3 |
| SAMHD1 |
| SAR1A |
| SARAF |
| SART3 |
| SATB1 |
| SATB1-AS1 |
| SCARB1 |
| SCML4 |
| SDHA |
| SDK1 |
| SDK2 |
| SEC14L1 |
| SELL |
| SEMA3E |
| SEMA4B |
| SEMA4D |
| SERINC5 |
| SERP2 |
| SERPINE2 |
| SERTAD2 |
| SESN2 |
| SETBP1 |
| SETD2 |
| SFMBT2 |
| SFSWAP |
| SFXN1 |
| SGCA |
| SGK1 |
| SGK223 |
| SGMS1 |
| SGSM3 |
| SH2B3 |
| SH3BP2 |
| SH3BP5 |
| SH3PXD2A |
| SH3RF2 |
| SH3TC1 |
| SIK1 |
| SIK3 |
| SIL1 |
| SKI |
| SKIDA1 |
| SLC11A2 |
| SLC12A7 |
| SLC12A8 |
| SLC1A2 |
| SLC20A1 |

TABLE 1-continued

| Human DNMT3A target genes |
|---|
| SLC24A2 |
| SLC25A12 |
| SLC25A25 |
| SLC25A33 |
| SLC25A44 |
| SLC30A7 |
| SLC37A1 |
| SLC38A1 |
| SLC3A1 |
| SLC7A5P1 |
| SLC7A6 |
| SLCO3A1 |
| SLCO4C1 |
| SLFN12 |
| SLFN12L |
| SMAD3 |
| SMARCA2 |
| SMARCB1 |
| SMG1P2 |
| SMPD1 |
| SMPD3 |
| SMU1 |
| SNAP47 |
| SND1 |
| SNHG5 |
| SNRK |
| SNX9 |
| SOCS1 |
| SOCS2 |
| SORCS2 |
| SORL1 |
| SPAG4 |
| SPAG9 |
| SPANXN3 |
| SPATA13 |
| SPATA3 |
| SPATA5 |
| SPECC1L-ADORA2A |
| SPEF2 |
| SPEN |
| SPOCD1 |
| SPOCK2 |
| SPPL3 |
| SPRED2 |
| SPRY1 |
| SPTBN1 |
| SPTLC2 |
| SREBF2 |
| SRGN |
| SRP14 |
| SRP14-AS1 |
| SSBP3 |
| SSBP4 |
| SSC4D |
| SSSCA1 |
| ST3GAL1 |
| ST3GAL2 |
| ST3GAL3 |
| ST3GAL5 |
| ST6GAL1 |
| ST7 |
| ST8SIA4 |
| ST8SIA6 |
| STAG3 |
| STAMBPL1 |
| STAT1 |
| STAT5A |
| STAT5B |
| STK17A |
| STK17B |
| STK24 |
| STK31 |
| STK32C |
| STK38 |
| STK39 |
| STK4 |
| STK40 |
| STRADA |

TABLE 1-continued

| Human DNMT3A target genes |
|---|
| STX10 |
| SUMO1P1 |
| SUSD3 |
| SVIL |
| SYK |
| SYNJ2 |
| SYPL1 |
| SYTL2 |
| TAB2 |
| TAF1B |
| TAF4 |
| TAGAP |
| TARBP 1 |
| TBC1D1 |
| TBC1D14 |
| TBC1D5 |
| TBL1X |
| TBL1XR1 |
| TCF20 |
| TCF7 |
| TEC |
| TERT |
| TESPA1 |
| TET3 |
| TFAP2A |
| TG |
| TGFBR1 |
| TGFBR2 |
| TGFBR3 |
| TGIF2LX |
| TH2LCRR |
| THRA |
| TIAM1 |
| TIMM23B |
| TIMP2 |
| TKTL1 |
| TLDC1 |
| TLE3 |
| TLE4 |
| TLK1 |
| TLR9 |
| TMC6 |
| TMCC1 |
| TMCC2 |
| TMCO5A |
| TMEM110 |
| TMEM123 |
| TMEM161B |
| TMEM163 |
| TMEM261 |
| TMEM263 |
| TMEM30B |
| TMEM63A |
| TMEM65 |
| TMEM92-AS1 |
| TMIGD3 |
| TMPRSS13 |
| TNFAIP8 |
| TNFRSF10A |
| TNFRSF8 |
| TNFSF4 |
| TNP2 |
| TNPO1 |
| TNRC6B |
| TNRC6C |
| TNS4 |
| TOM1L2 |
| TOMM20 |
| TOP2B |
| TOX |
| TOX2 |
| TP53INP1 |
| TPCN1 |
| TPM4 |
| TPST2 |
| TPTE |
| TRA2A |
| TRABD2A |

TABLE 1-continued

| Human DNMT3A target genes |
| --- |
| TRAF1 |
| TRAF3IP2 |
| TRAF3IP2-AS1 |
| TRAF3IP3 |
| TRAF5 |
| TRAK1 |
| TRAPPC10 |
| TRAPPC9 |
| TREML2 |
| TRERF1 |
| TRIB1 |
| TRIM46 |
| TRIO |
| TRPC6 |
| TRPM8 |
| TRPS1 |
| TSC22D2 |
| TSHR |
| TSHZ2 |
| TSNAX-DISC1 |
| TSPAN14 |
| TSPAN17 |
| TSPAN2 |
| TSPAN5 |
| TSSC1 |
| TTC34 |
| TTC39C |
| TTC7A |
| TTC9 |
| TUSC5 |
| TXK |
| UBAC2 |
| UBAP2L |
| UBE2B |
| UBE2E1 |
| UBE2E1-AS1 |
| UBE2G2 |
| UBE2H |
| UCP2 |
| UHRF1BP1 |
| ULK4 |
| UPF2 |
| URGCP-MRPS24 |
| USP10 |
| USP12 |
| USP20 |
| USP3 |
| USP35 |
| UTRN |
| VAC14 |
| VAMP4 |
| VAMP5 |
| VAV3 |
| VAV3-AS1 |
| VGLL4 |
| VOPP1 |
| VPS37B |
| VPS45 |
| VPS53 |
| VWF |
| WASF2 |
| WBP1L |
| WDFY2 |
| WDR1 |
| WDR72 |
| WIPF1 |
| WISP3 |
| WT1 |
| WWOX |
| XBP1 |
| XYLT1 |
| YWHAE |
| ZAP70 |
| ZBP1 |
| ZBTB16 |
| ZBTB34 |
| ZC3H3 |
| ZCCHC2 |

TABLE 1-continued

| Human DNMT3A target genes |
| --- |
| ZDHHC14 |
| ZEB2 |
| ZFHX3 |
| ZFP36L2 |
| ZFX |
| ZFYVE21 |
| ZFYVE28 |
| ZHX2 |
| ZHX3 |
| ZIC3 |
| ZMAT4 |
| ZMIZ1 |
| ZMPSTE24 |
| ZNF124 |
| ZNF217 |
| ZNF318 |
| ZNF335 |
| ZNF395 |
| ZNF414 |
| ZNF438 |
| ZNF445 |
| ZNF496 |
| ZNF609 |
| ZNF683 |
| ZNF775 |
| ZNF831 |
| ZNF862 |
| ZNRF1 |

As shown in FIG. 1, patients with a Complete Response (CR), Partial Response (PR), and Partial Response with Relapse (PRtd) on average have higher relative expression of DNMT3A targets in comparison to patients who exhibited No Response (NR). This indicates that, cumulatively, the target genes identified as DNMT3A methylation targets in the CAR experiments are more highly expressed in patients who responded to CART cell therapy. Based on the explanation of previous methylation experiments that led to this list of targets, these genes are also expected to be more highly expressed in DNMT3A-knockout CAR T cells. Importantly, the differences visualized in FIG. 1 are statistically significant both when considering all conditions simultaneously (Kruskal Wallis non-parametric ANOVA, $p=0.00988$) or when specifically comparing CR to NR (Mann-Whitney U Test, $p=0.009851$). Since responders also had a 65- to 635-fold greater expansion in comparison to non-responders, these data highlight that the expansion potential of T cells is closely linked to expression of DNMT3A-targeted genes.

Figure 2:
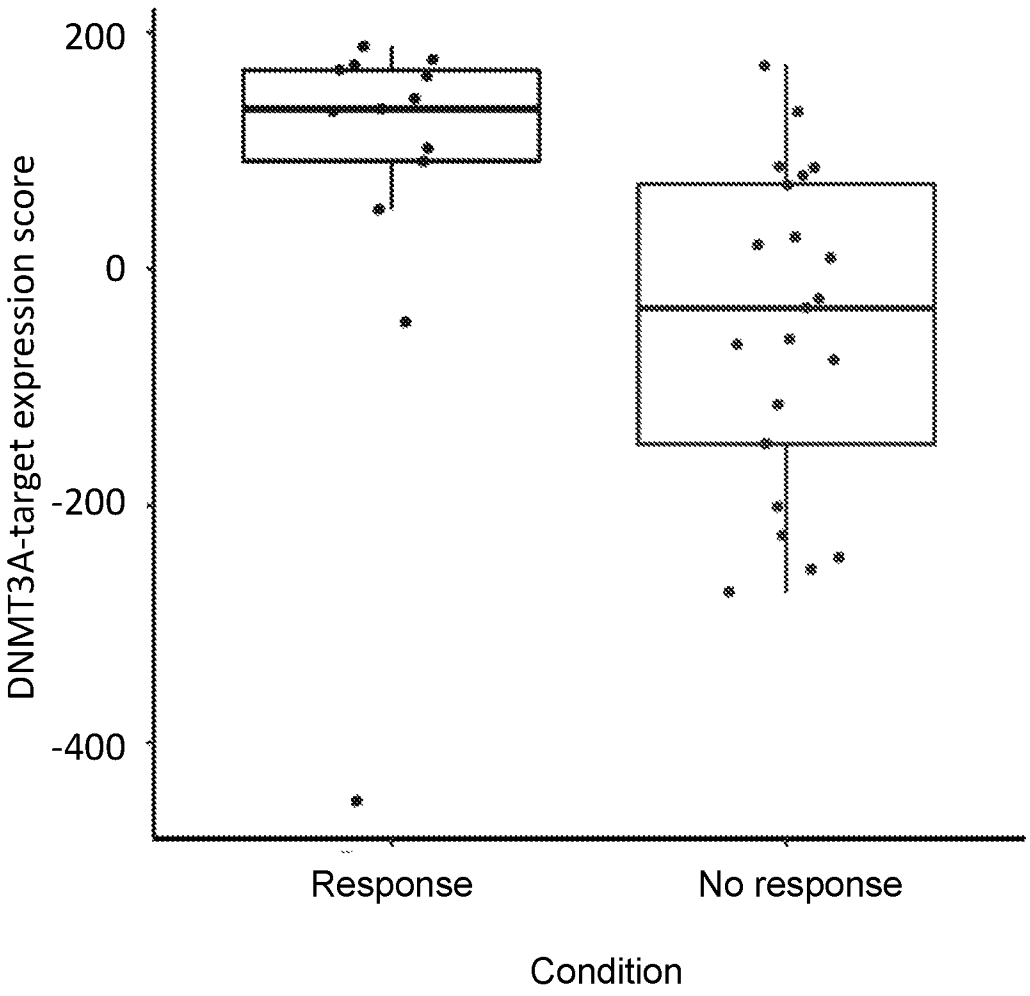
FIG. 2 is a plot showing the comparison of the expression score of DNMT3A target genes in the CAR T-cell products prior to infusion between patients who exhibited any type of response and no response.

Because Complete Response (CR) was not significantly different from either of the Partial Response (PR) groups (CR-vs-PR: $p=0.3095$; CR-vs-PRtd: $p=0.7857$), all patients who exhibited any type of response were also pooled and compared to No Response (NR) (see FIG. 2). Unsurprisingly, the difference between these two groups was also statistically significant ($p=0.001021$).

Figure 3:
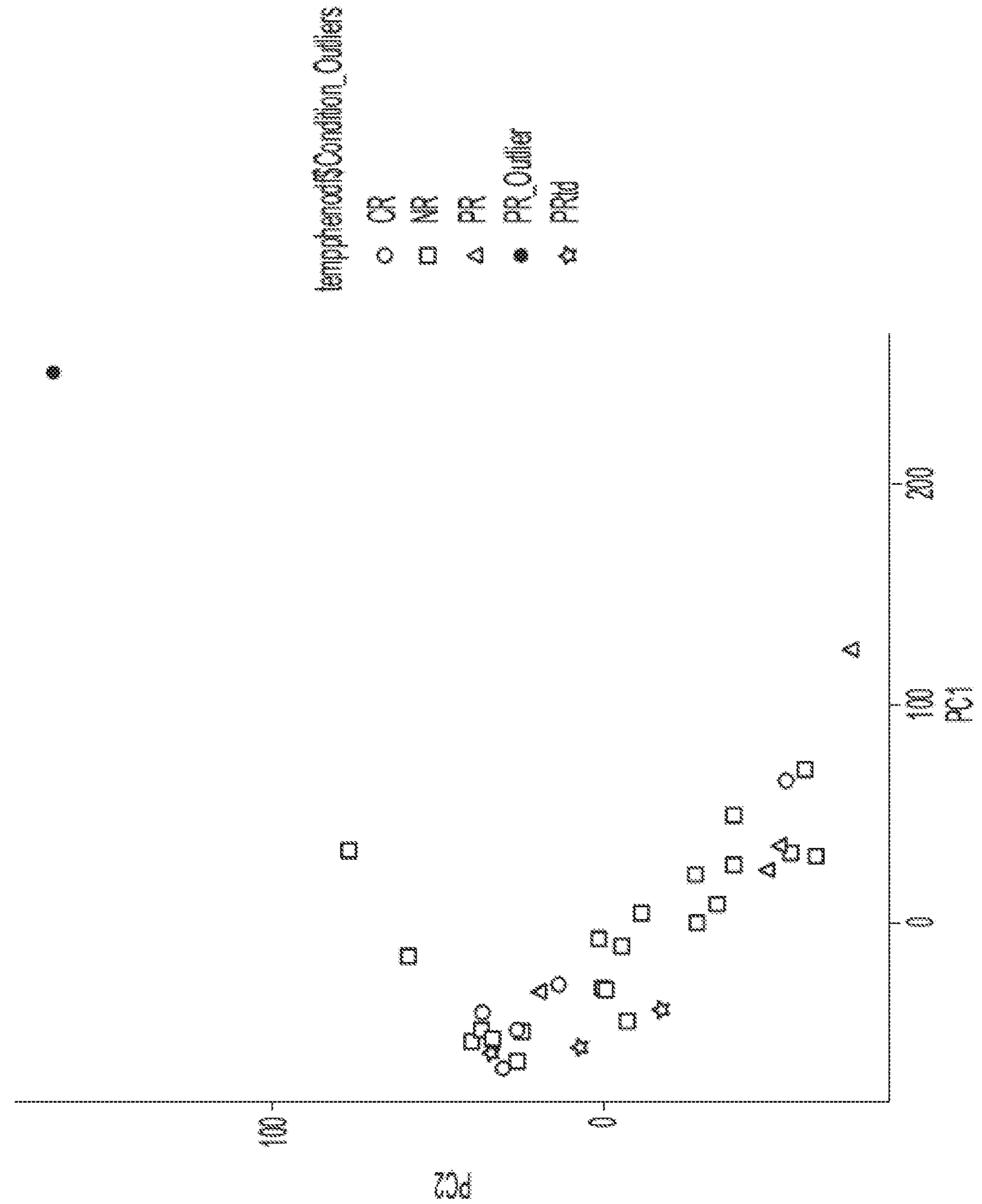
FIG. 3 shows an outlier in the data from a patient with a Partial Response (PR).
Figure 4:
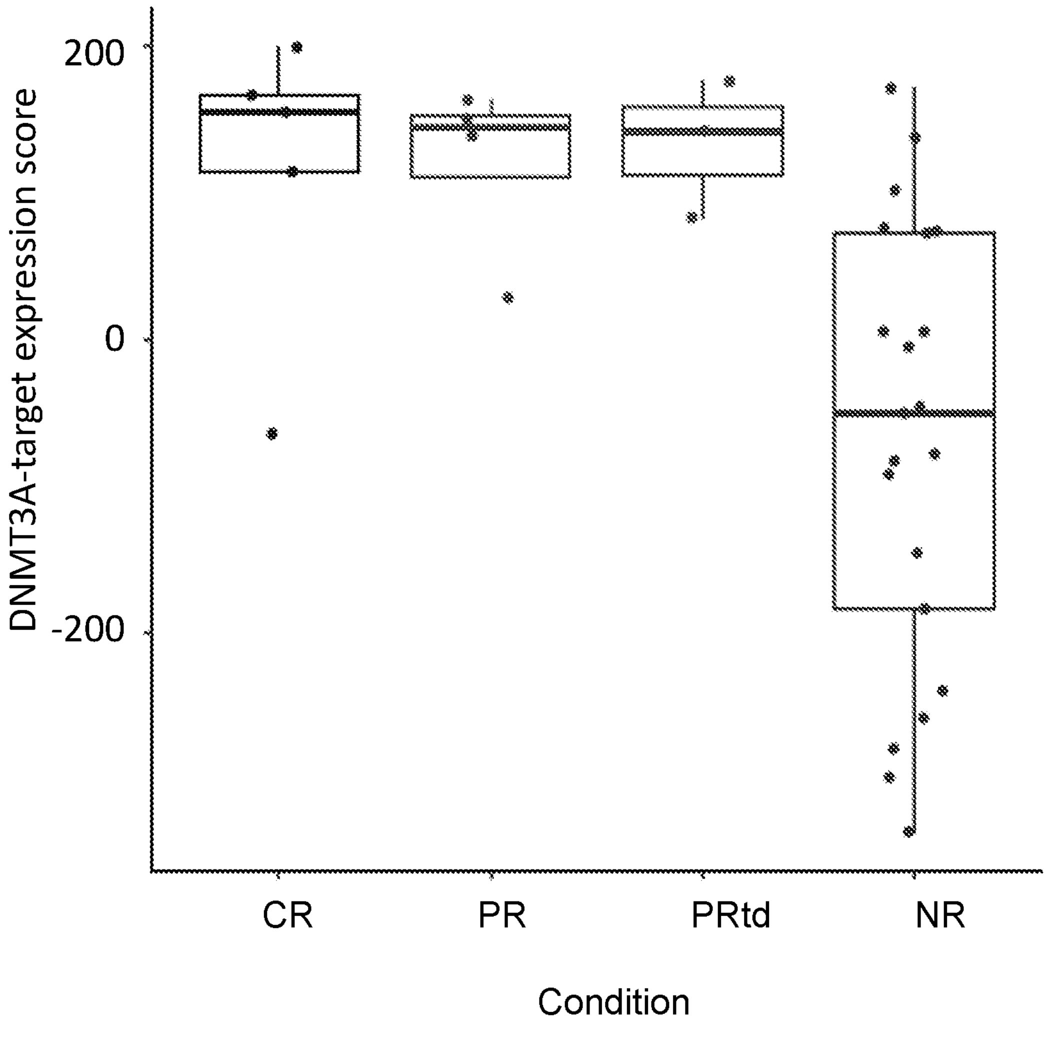
FIG. 4 is a plot showing the comparison of expression score of DNMT3A target genes in the CAR T-cell products prior to infusion between patients with a Complete Response (CR), Partial Response (PR), Partial Response with Relapse (PRtd), and No Response (NR) with the "outlier" data point excluded. p value between NR and PRtd<0.05; p value between NR and CR<0.01; p value between NR and PR<0.01.

Notably, there is an extreme outlier from a patient with a Partial Response (PR) (see FIG. 3, the point in the upper-right corner). However, the comparisons presented above are statistically significant even with the inclusion of this outlier. FIG. 4 shows the comparison with the "outlier" data point excluded. All of the comparisons remain significant.

Example 2. Gene Expression Signature with Limited List of DNMT3A Targets

A limited list of 107 genes (listed in Table 2) were selected from the list of DNMT3A targets. The selected genes showed log(fold change)>0.5 in the expected direction. The limited list allows improved predictive power of the test by excluding excess noise.

TABLE 2

| Selected subset of target genes |
|---|
| ACOXL |
| ADAMTS10 |
| ADRA2B |
| ANKRD53 |
| APBA2 |
| ATP10A |
| AUTS2 |
| BACH2 |
| BATF3 |
| BCL3 |
| BCL6 |
| C1QTNF4 |
| CA6 |
| CACNA2D3 |
| CAMK4 |
| CBLB |
| CD244 |
| CD27 |
| CDKL4 |
| CNTNAP5 |
| COL6A3 |
| CRIM1 |
| DGKD |
| DPF3 |
| DPP6 |
| EGR2 |
| EGR3 |
| EOMES |
| EPHB1 |
| FAM134B |
| FES |
| FLJ21408 |
| FOXP1 |
| FOXR1 |
| GIMAP4 |
| GPR55 |
| GRIK3 |
| HTRA4 |
| IFITM5 |
| IGSF9B |
| IL10 |
| IL18RAP |
| IL2RA |
| IL3 |
| INPP5A |
| IRX3 |
| ITM2C |
| LAMA3 |
| LINC00470 |
| LOC152225 |
| LY9 |
| LZTS1 |
| MACROD2 |
| MAML3 |
| MATN1 |
| MCTP2 |
| MDS2 |
| MGAT4A |
| MIR31HG |
| MYEOV |
| NELL2 |
| NR4A3 |
| NT5E |
| PEBP4 |
| PFKFB2 |
| PLAC8 |
| PLCL1 |
| PLXNA4 |
| PRR5 |
| PRRX2 |
| RASA3 |
| RGS6 |
| RIN3 |

TABLE 2-continued

| Selected subset of target genes |
|---|
| RNF157 |
| RTN4RL1 |
| SATB1 |
| SCML4 |
| SDK1 |
| SDK2 |
| SEMA3E |
| SETBP1 |
| SFMBT2 |
| SIK1 |
| SLC12A7 |
| SLC37A1 |
| SPRY1 |
| SSBP3 |
| STK31 |
| SVIL |
| TCF7 |
| TEC |
| TGFBR3 |
| TPTE |
| TRIO |
| TRPM8 |
| TTC34 |
| TTC39C |
| TXK |
| VAV3 |
| VWF |
| WISP3 |
| XYLT1 |
| ZBP1 |
| ZBTB16 |
| ZDHHC14 |
| ZMAT4 |
| ZNF683 |

Figure 5:
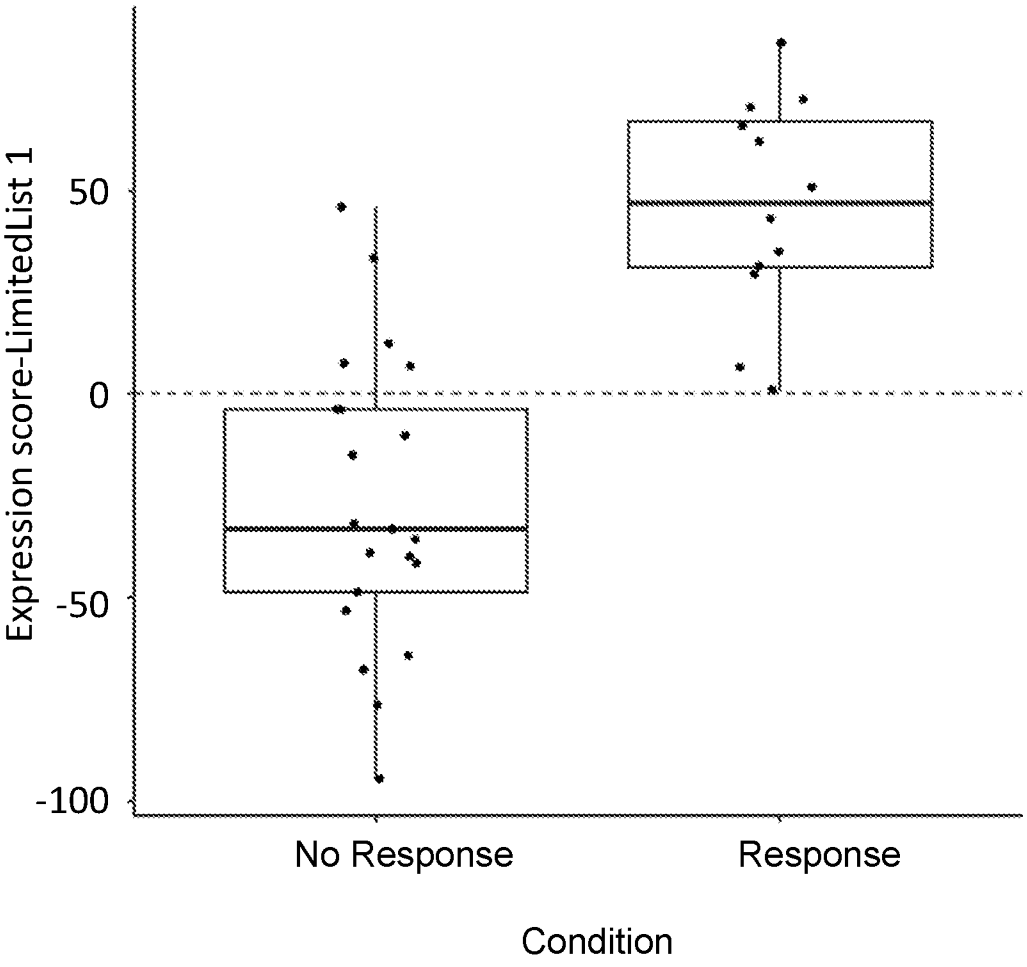
FIG. 5 is a plot showing the comparison of expression score of a limited list of target genes in the CAR T-cell products prior to infusion between patients who exhibited no response and any type of response.
Figure 6A:
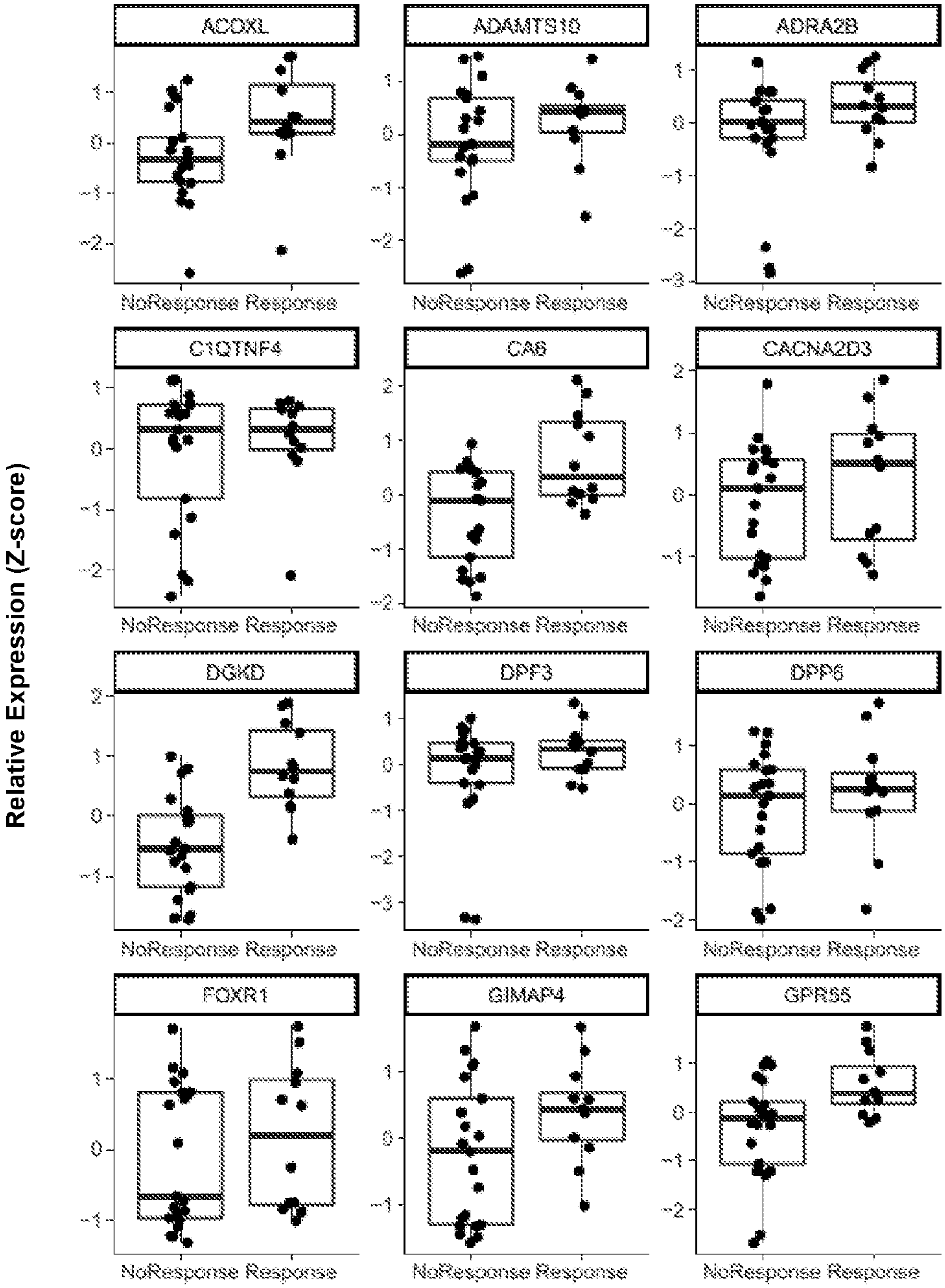
FIGS. 6A-6L show the relative expression (Z-score) of a limited list of target genes in the CAR T-cell products prior to infusion between patients who exhibited no response and any type of response.
Figure 6B:
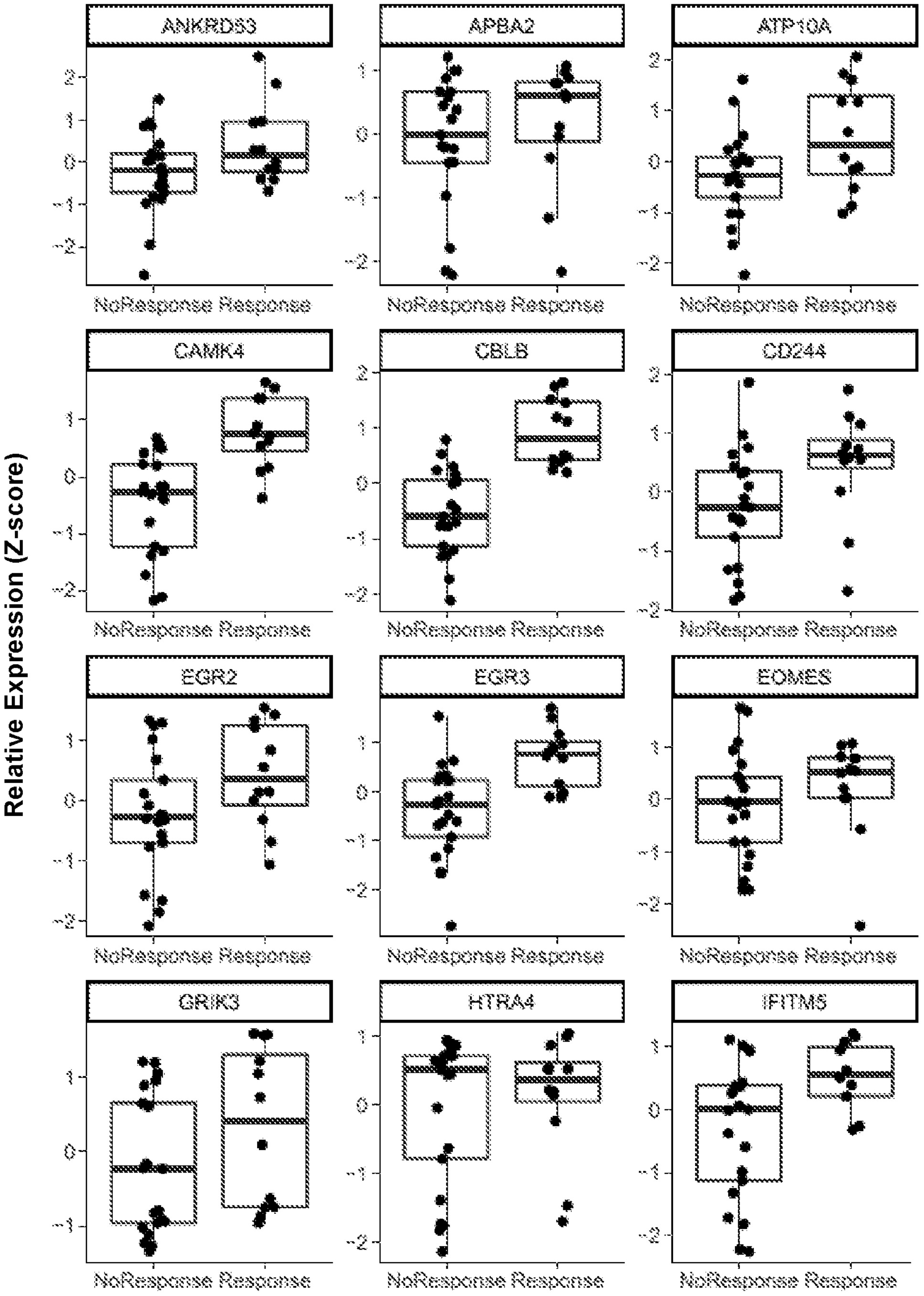
Figure 6C:
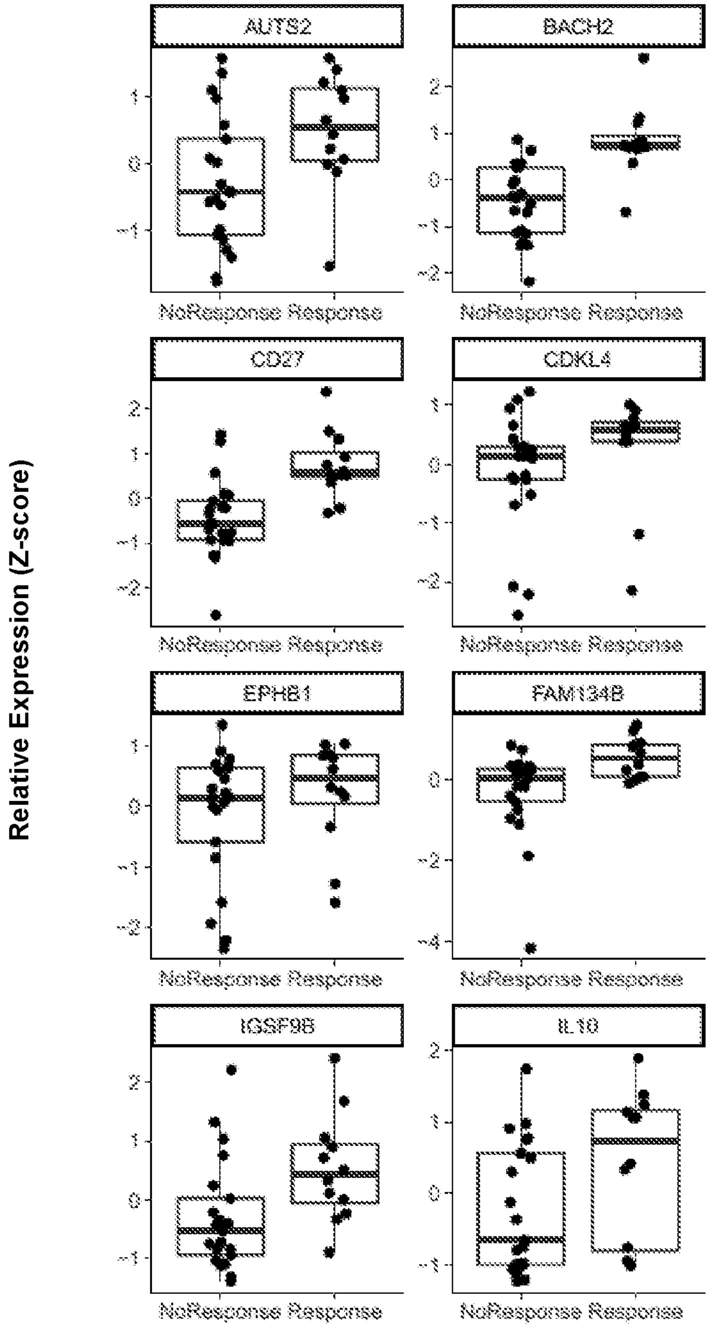
Figure 6D:
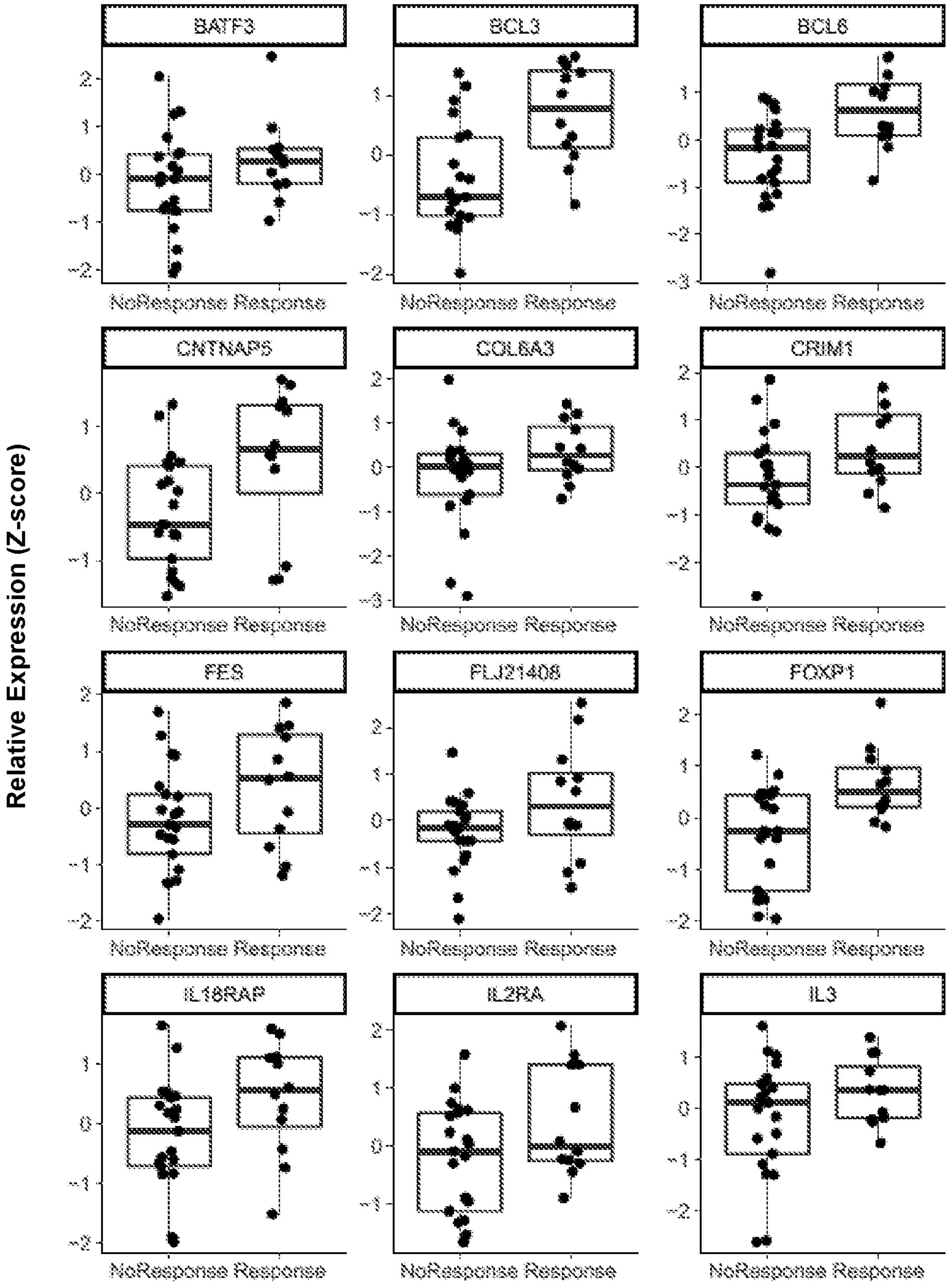
Figure 6E:
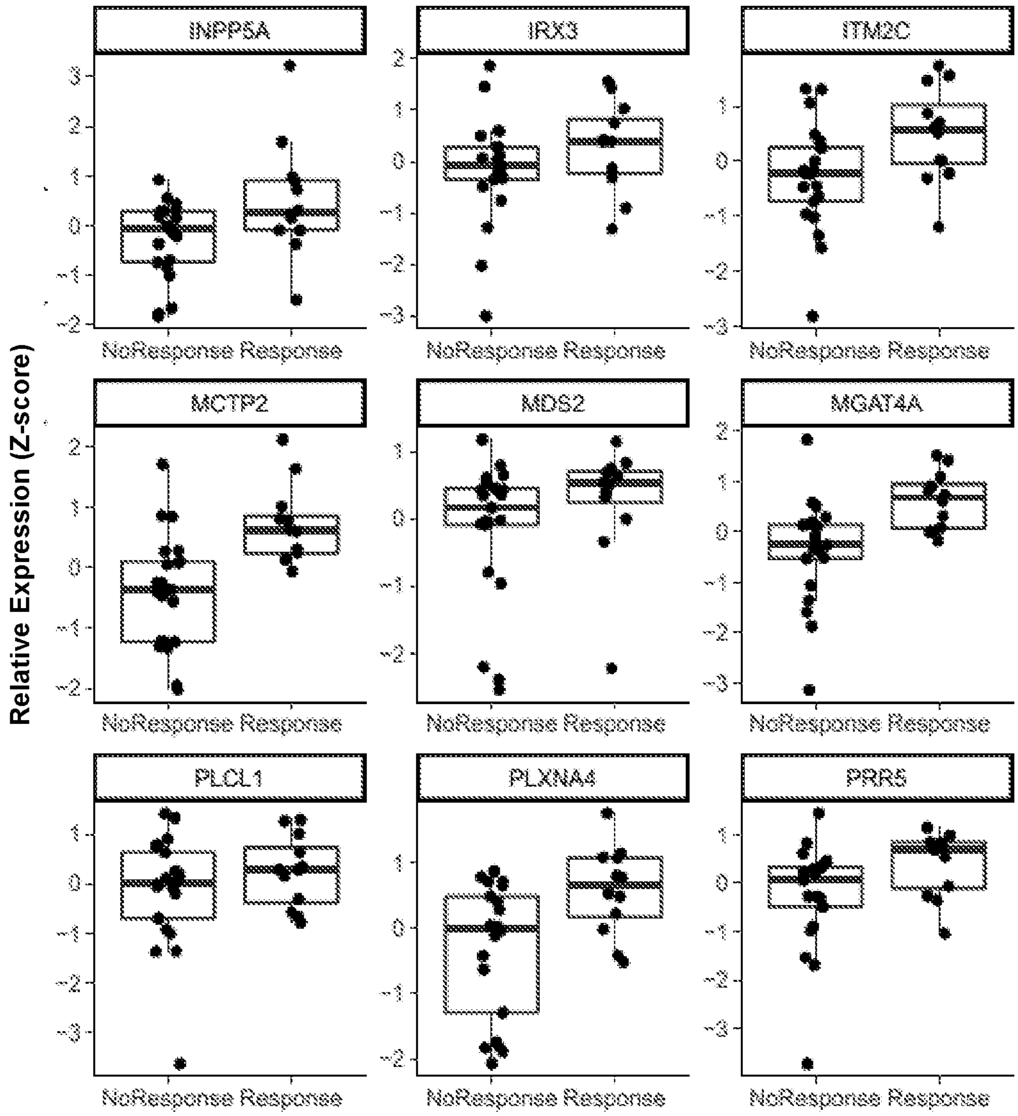
Figure 6F:
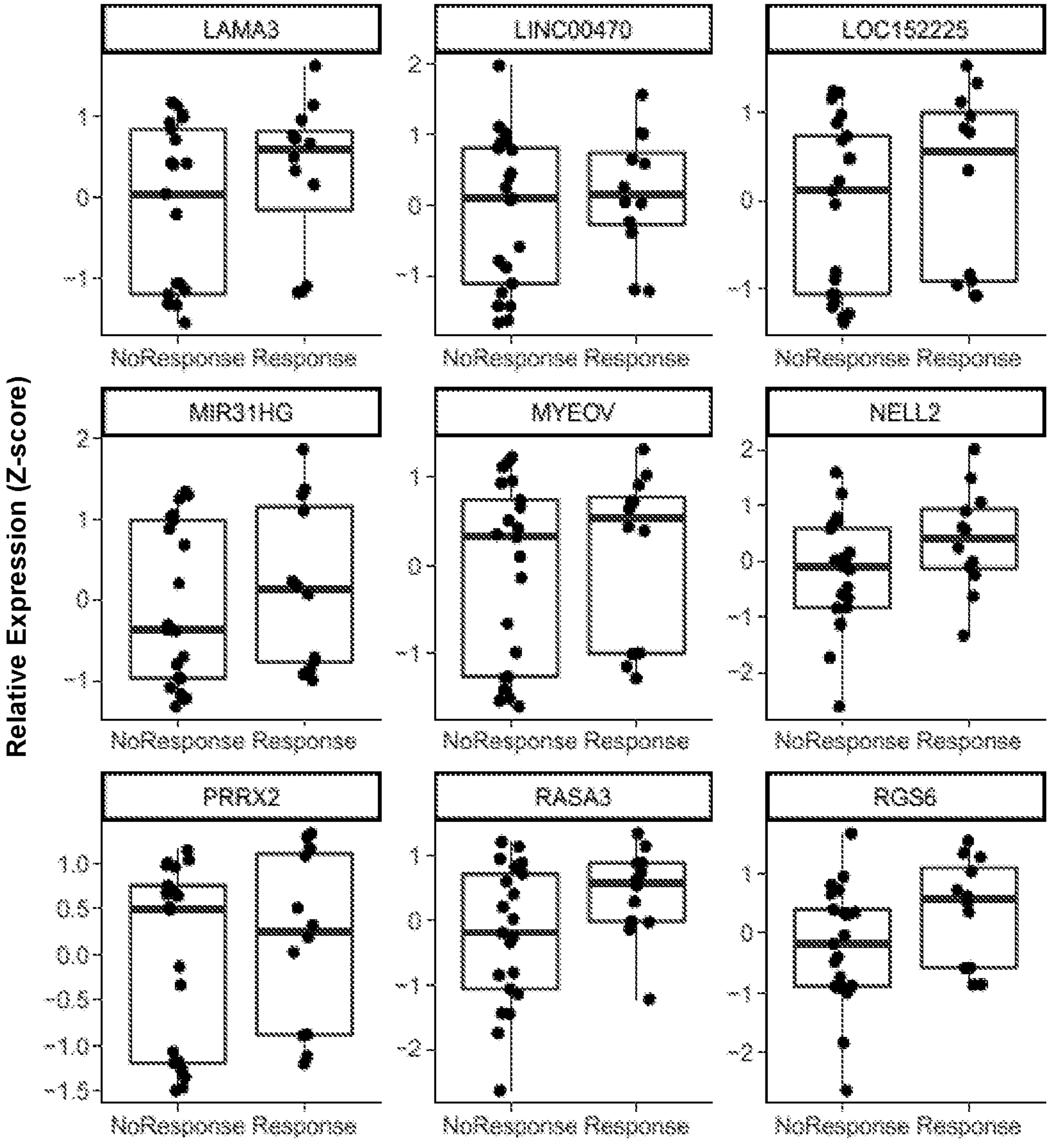
Figure 6G:
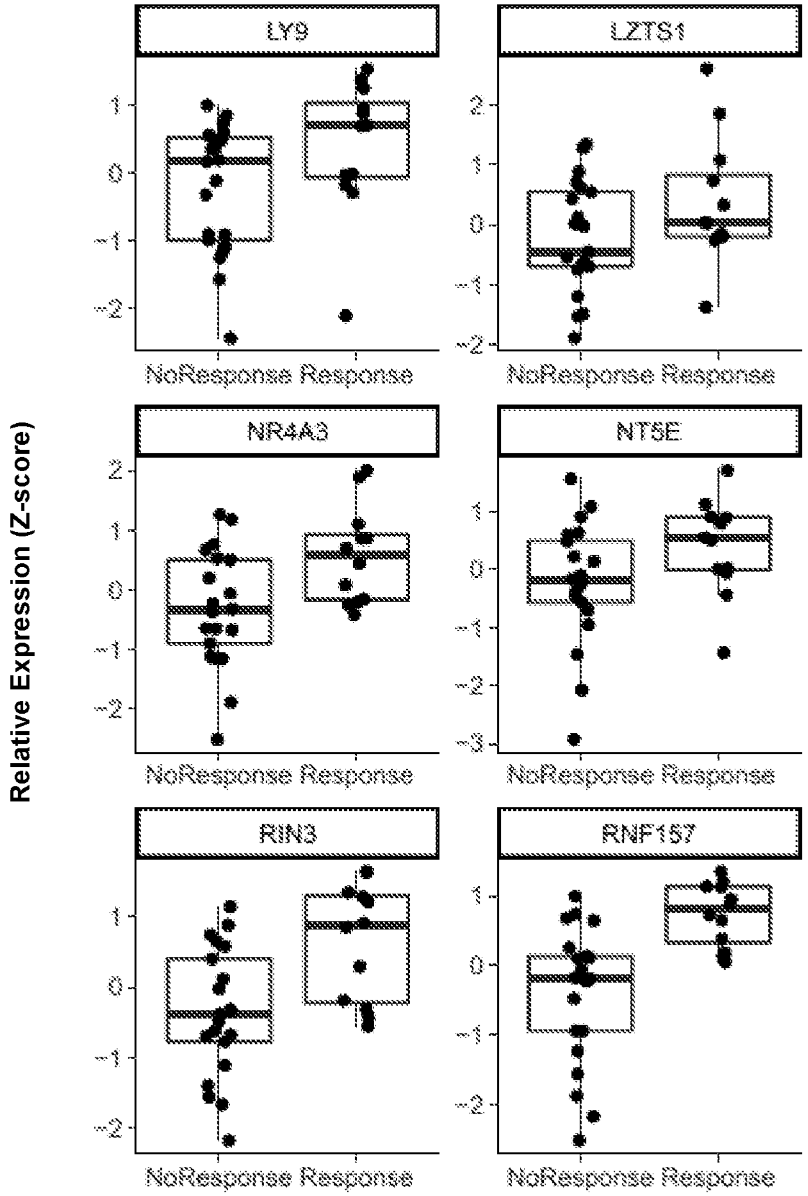
Figure 6H:
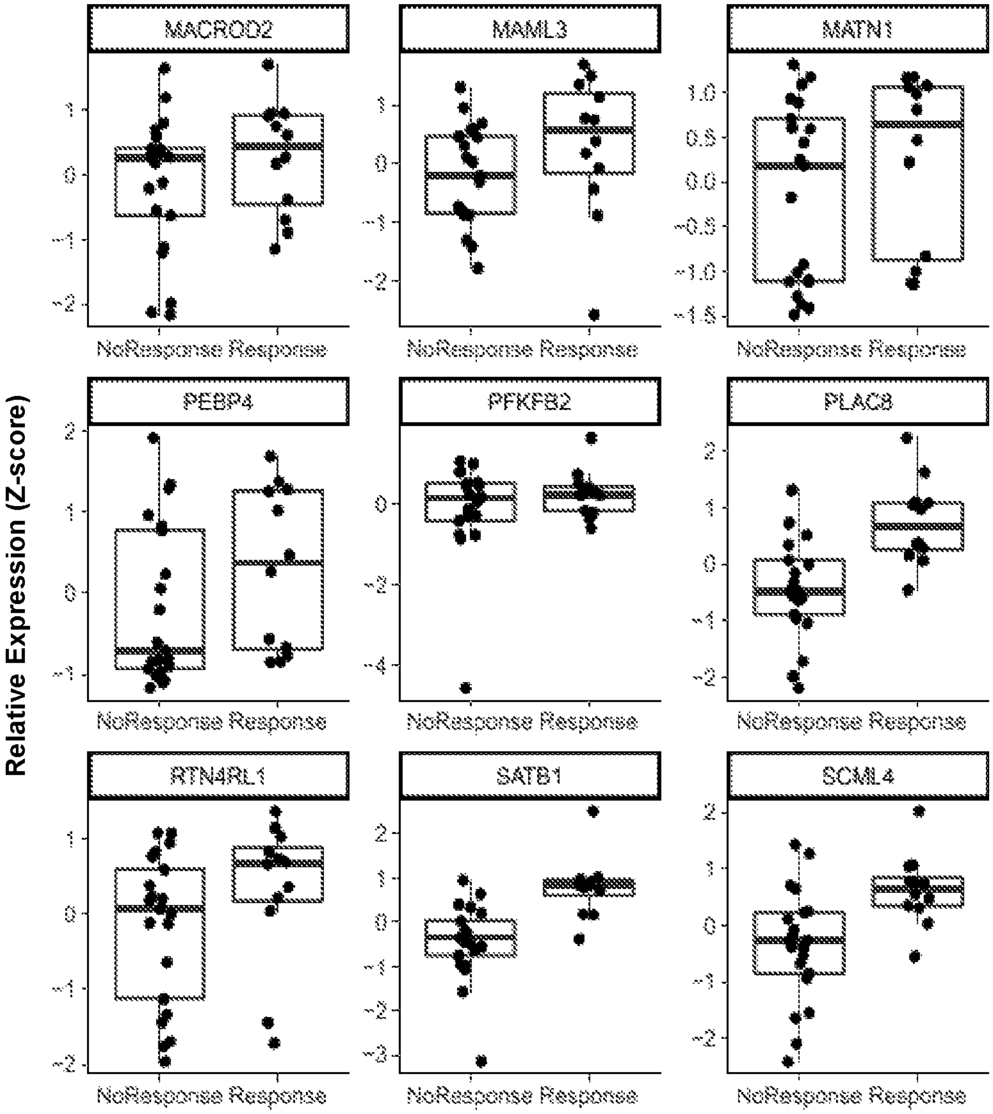
Figure 6I:
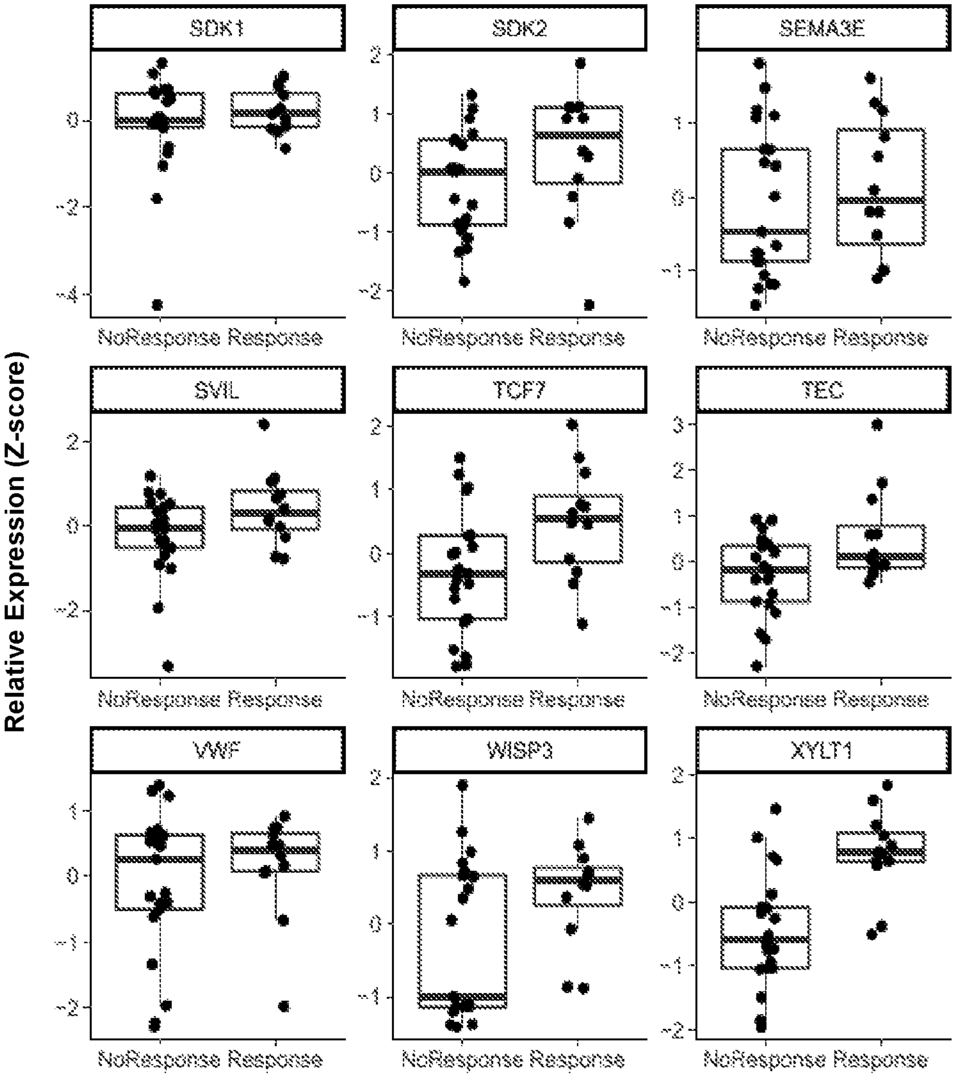
Figure 6J:
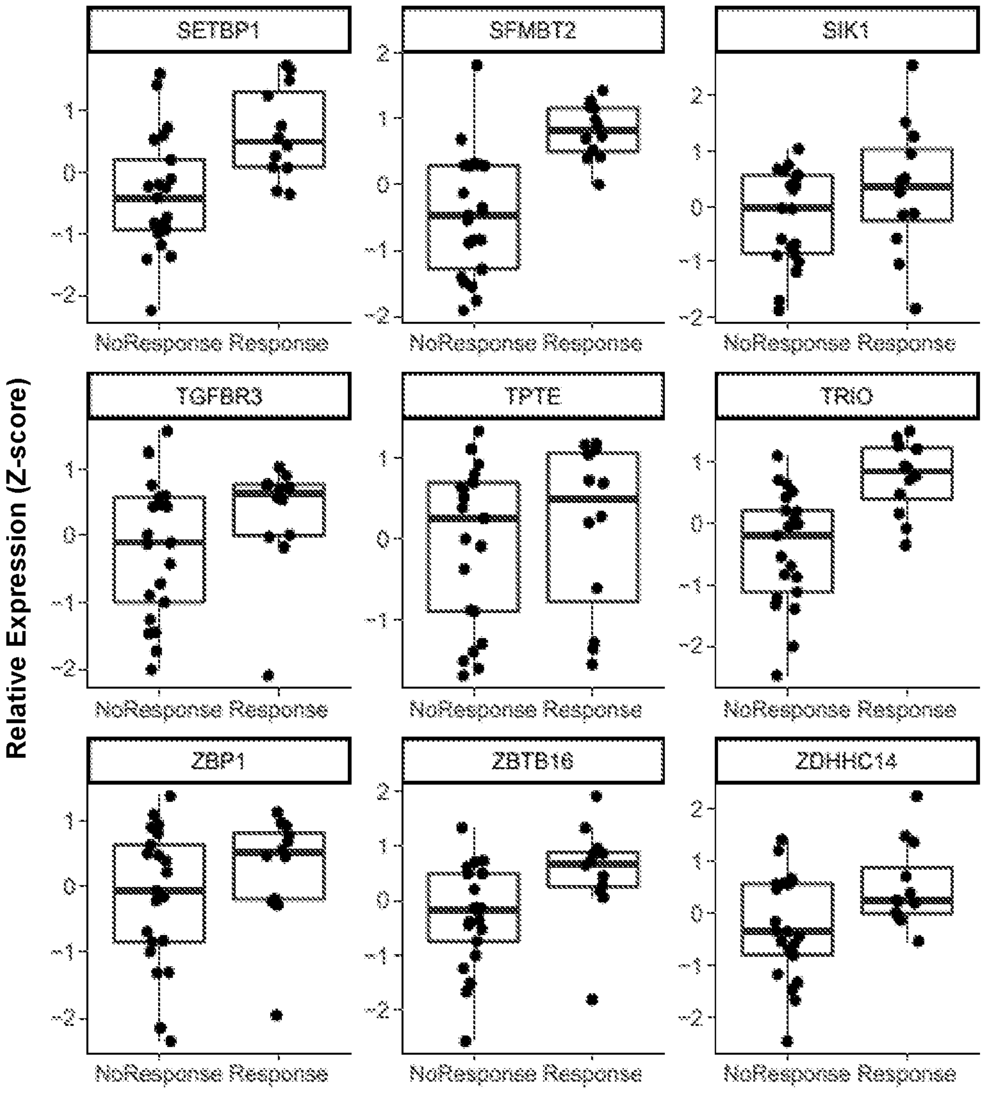
Figure 6K:
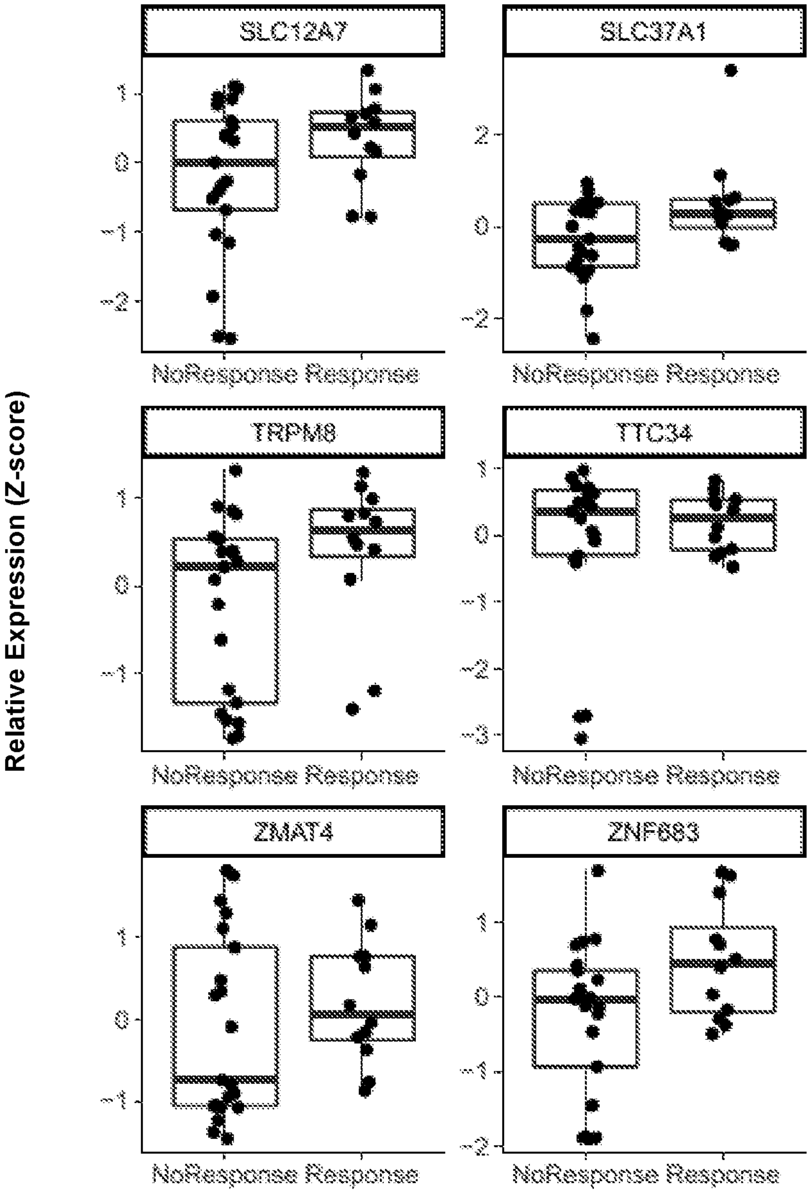
Figure 6L:
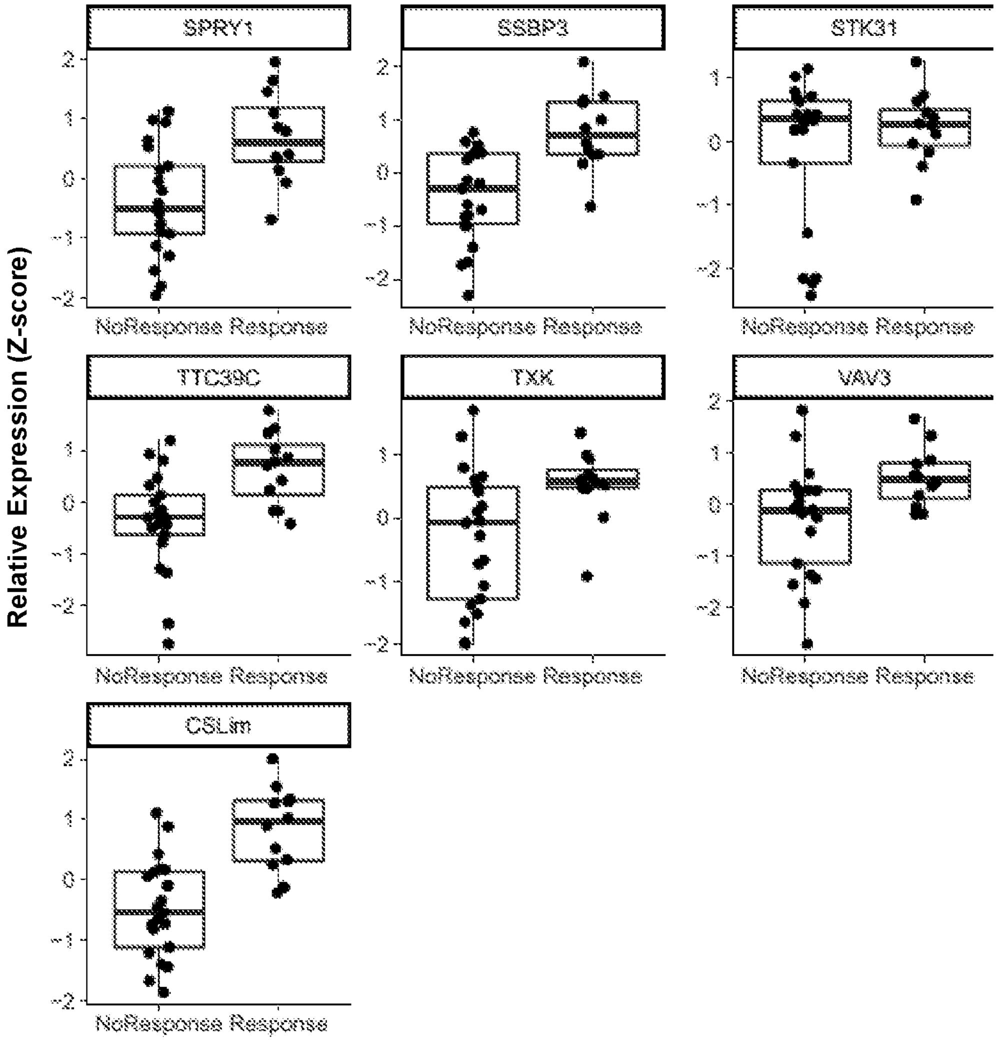
Figure 7A:
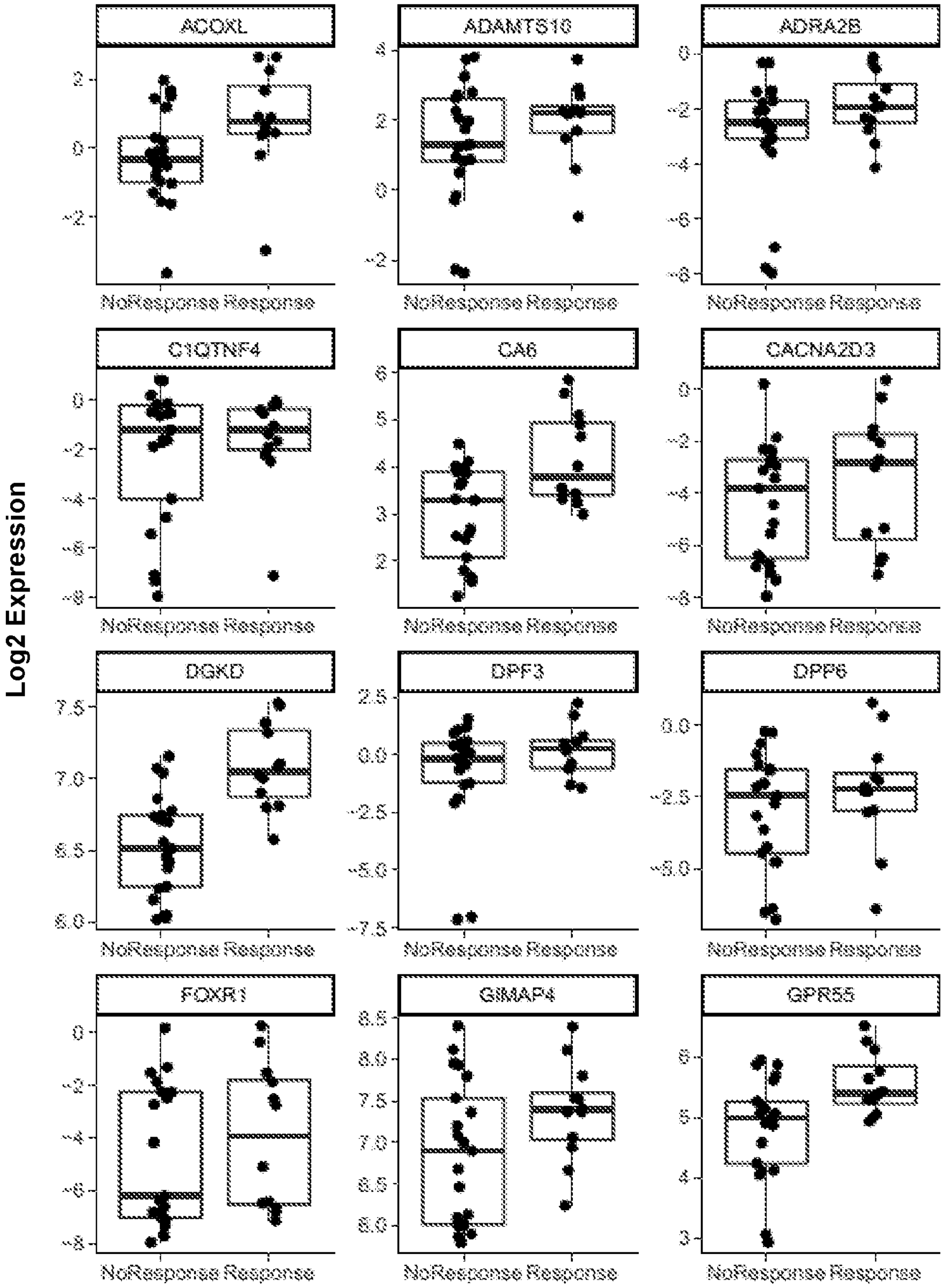
FIGS. 7A-7L show the absolute expression (log 2 value) of a limited list of target genes in the CAR T-cell products prior to infusion between patients who exhibited no response and any type of response.
Figure 7B:
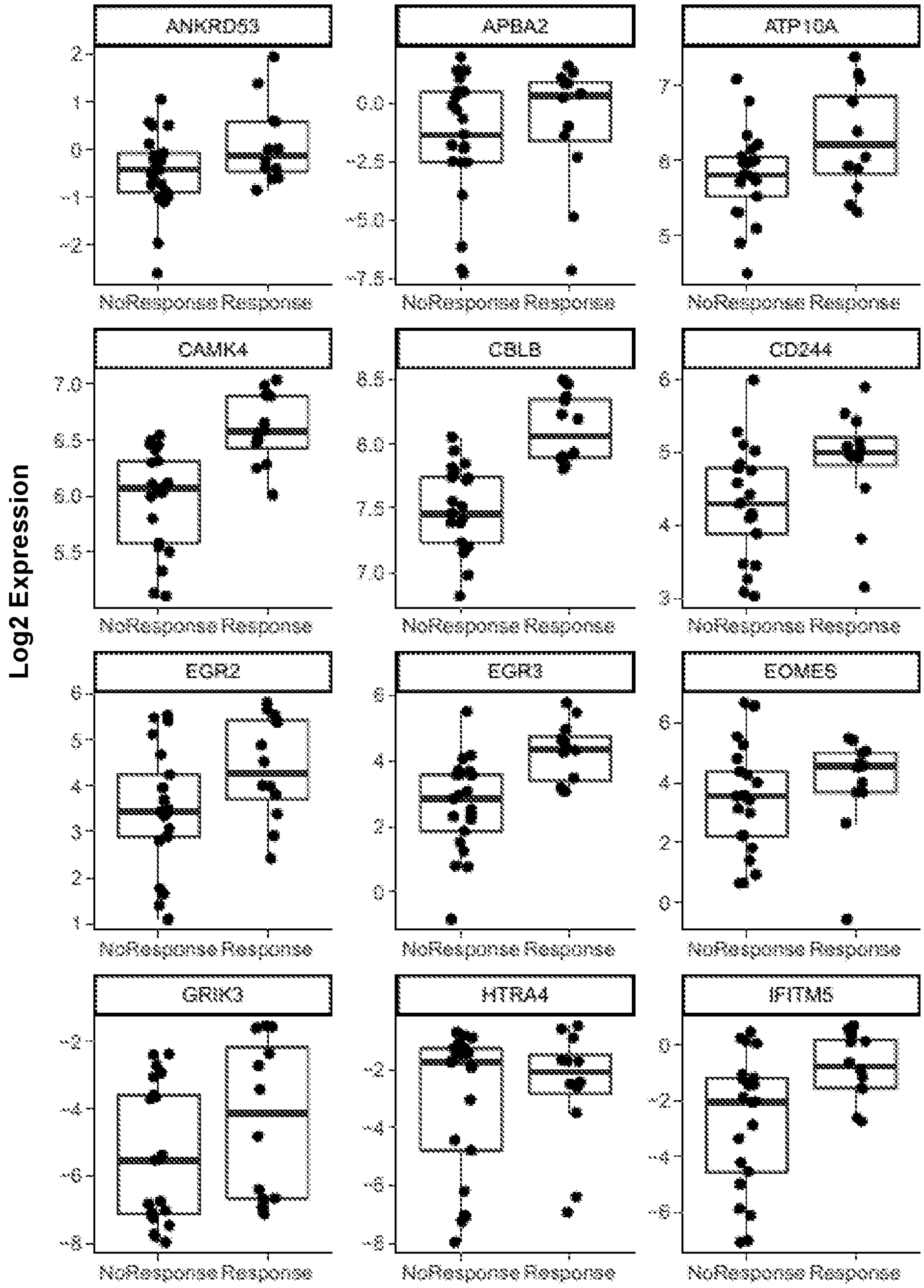
Figure 7C:
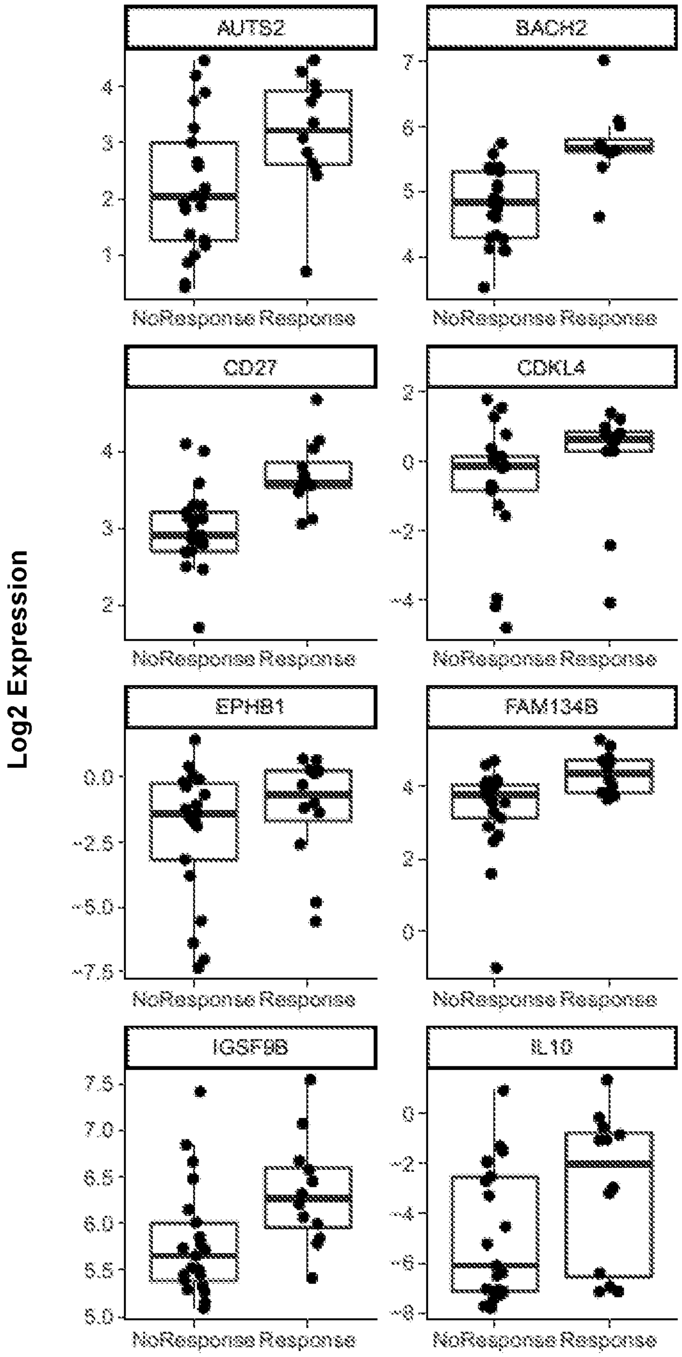
Figure 7D:
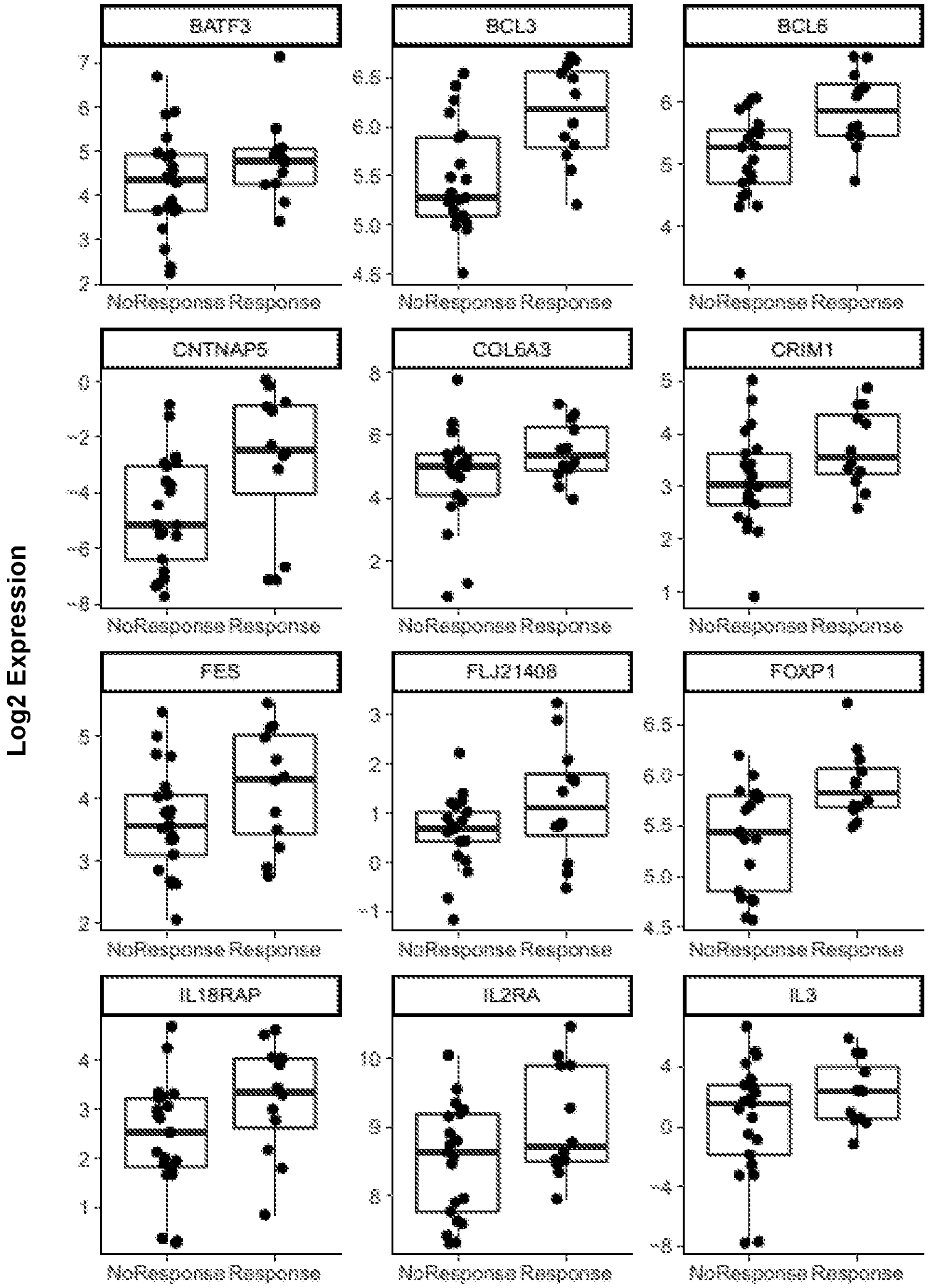
Figure 7E:
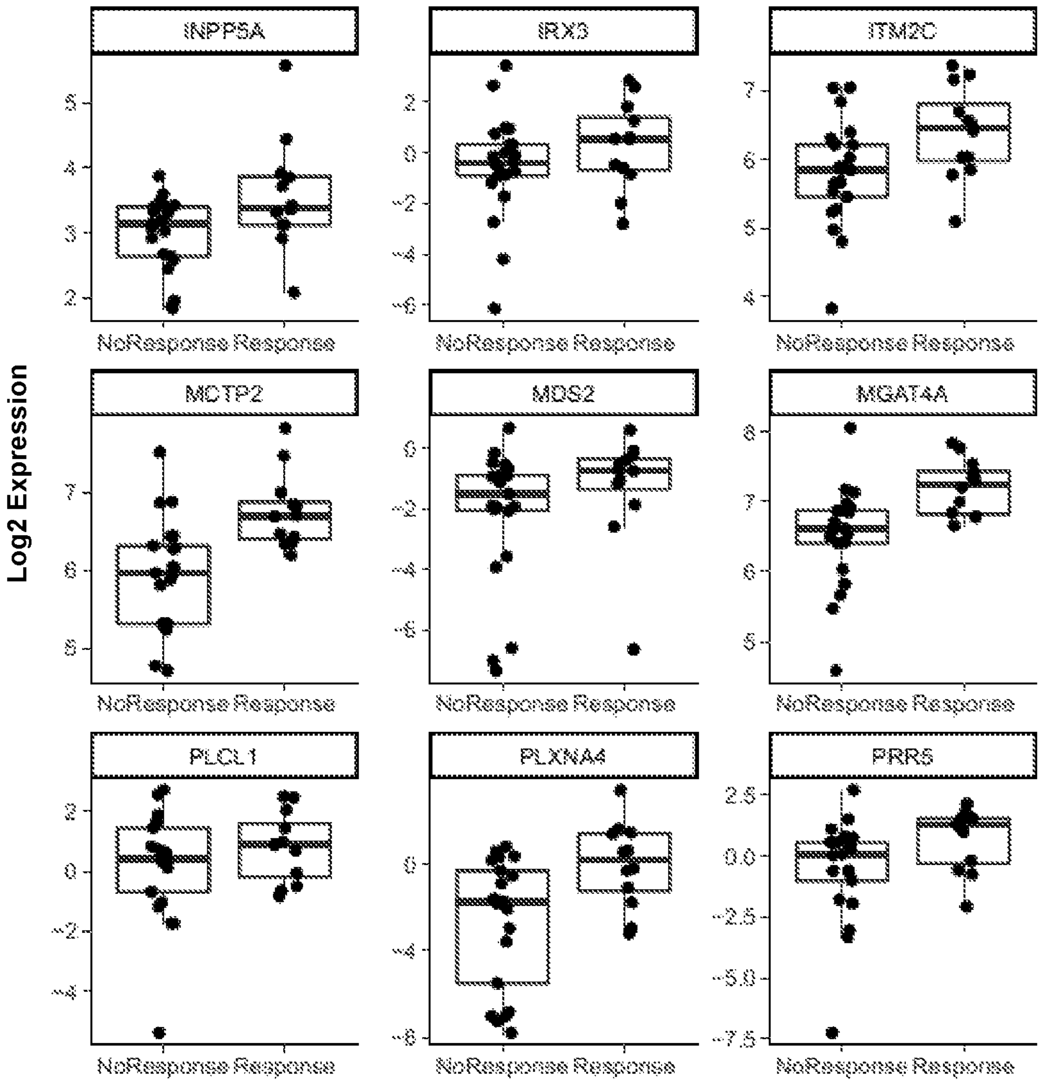
Figure 7F:
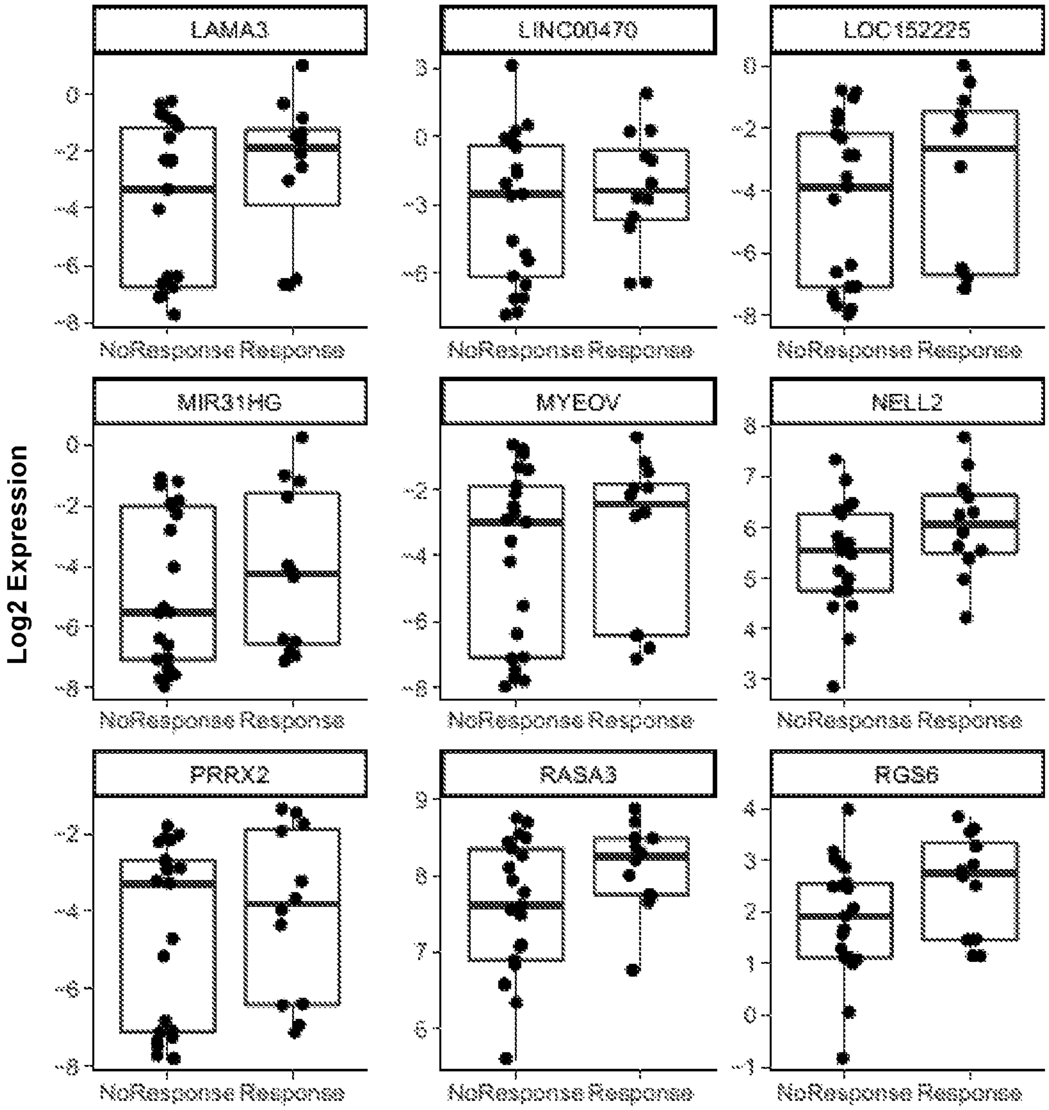
Figure 7G:
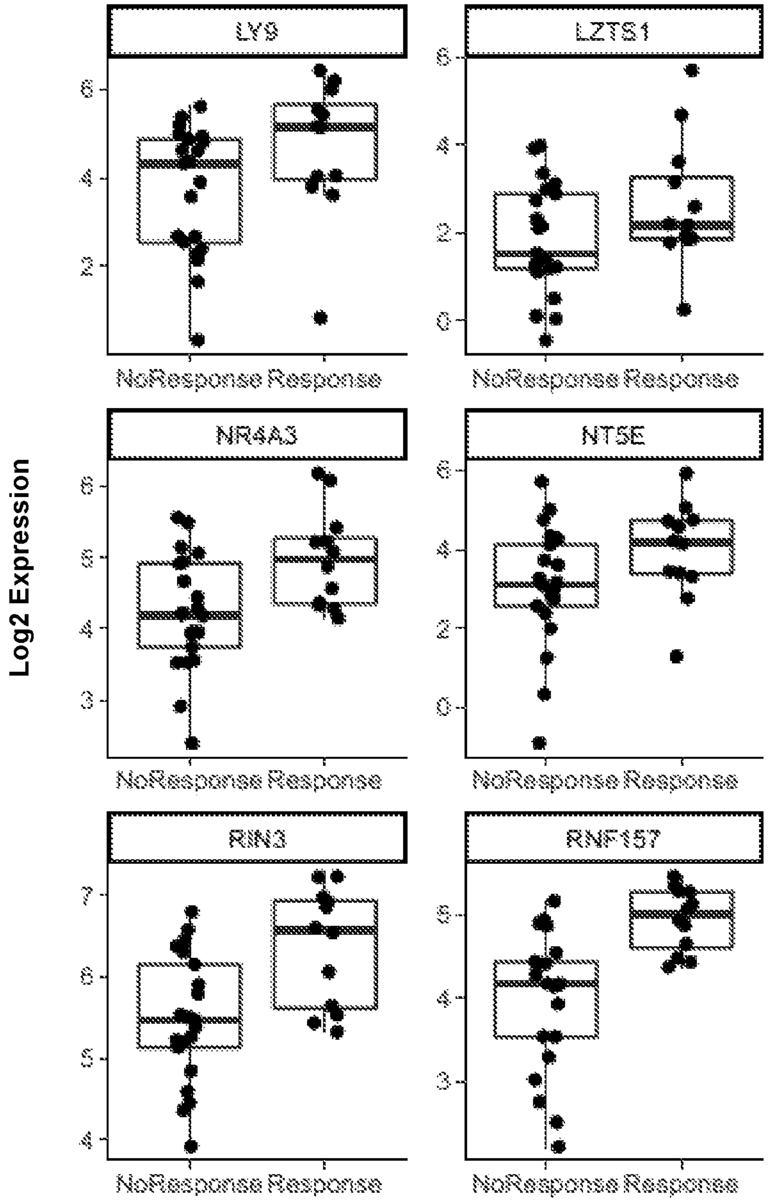
Figure 7H:
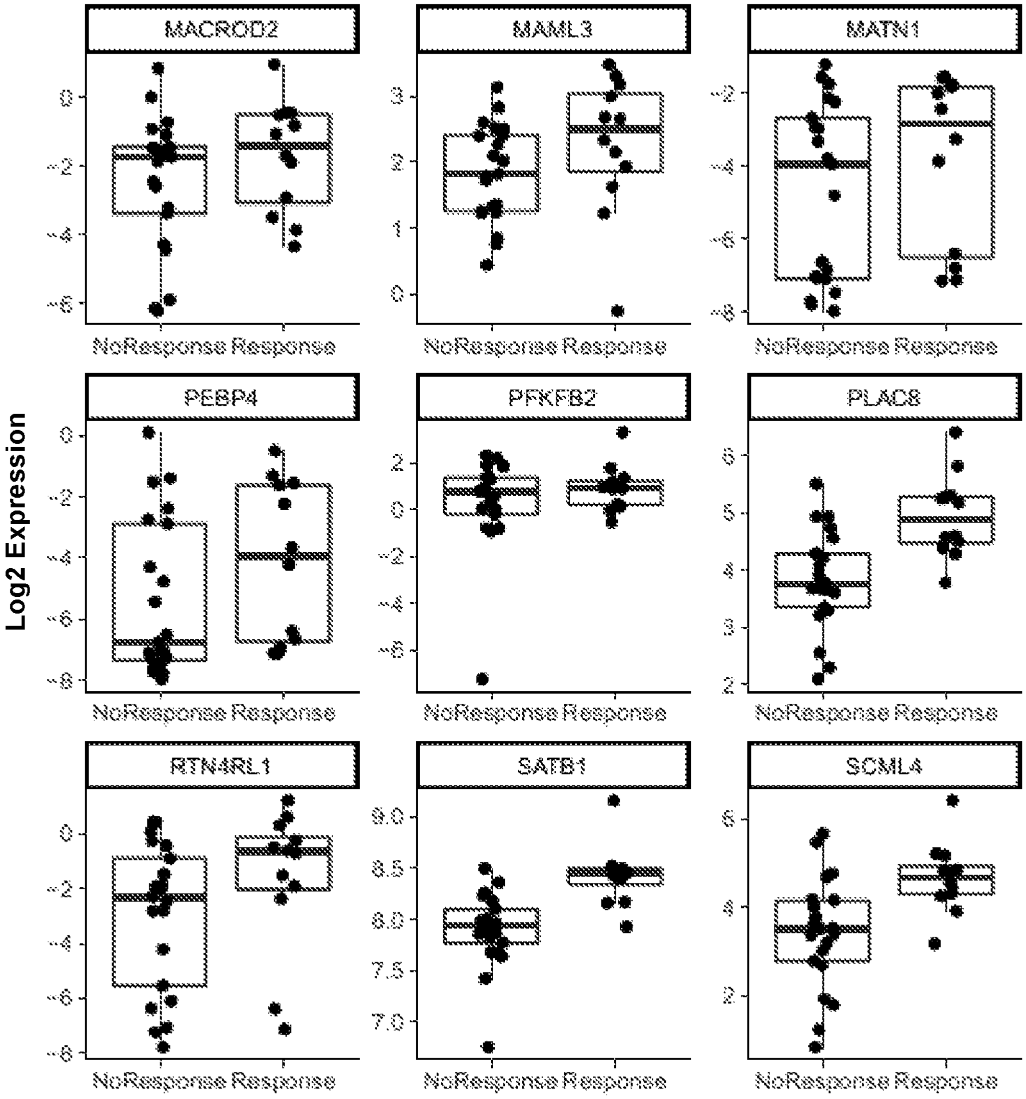
Figure 7I:
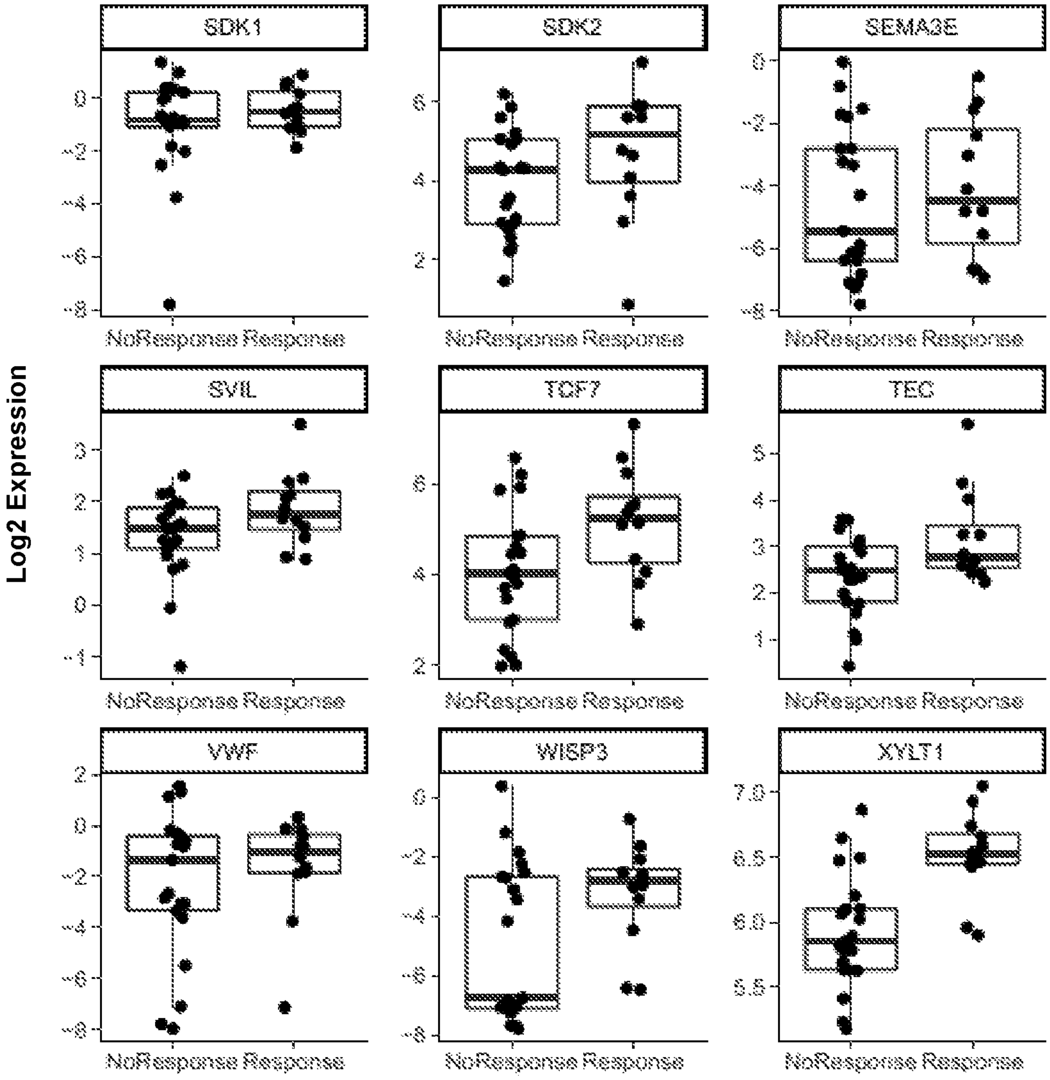
Figure 7J:
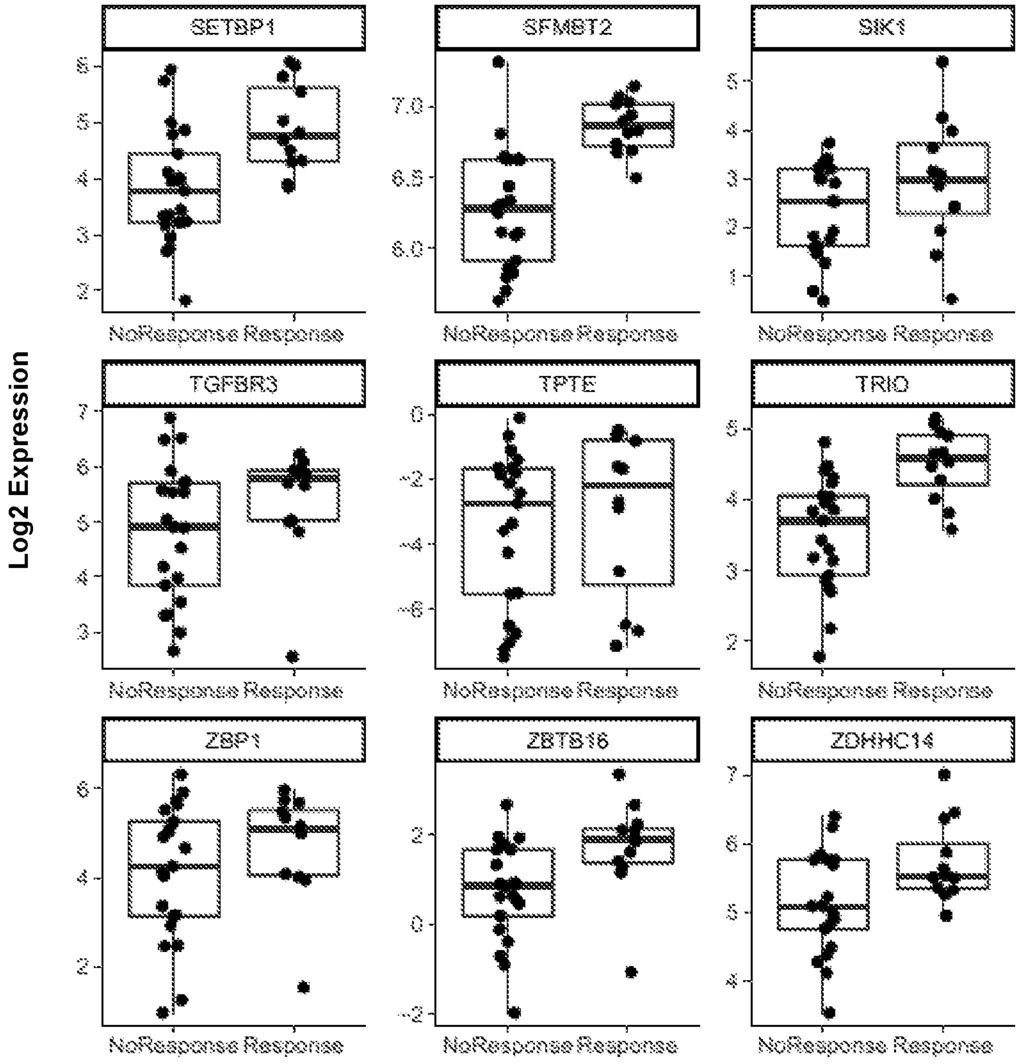
Figure 7K:
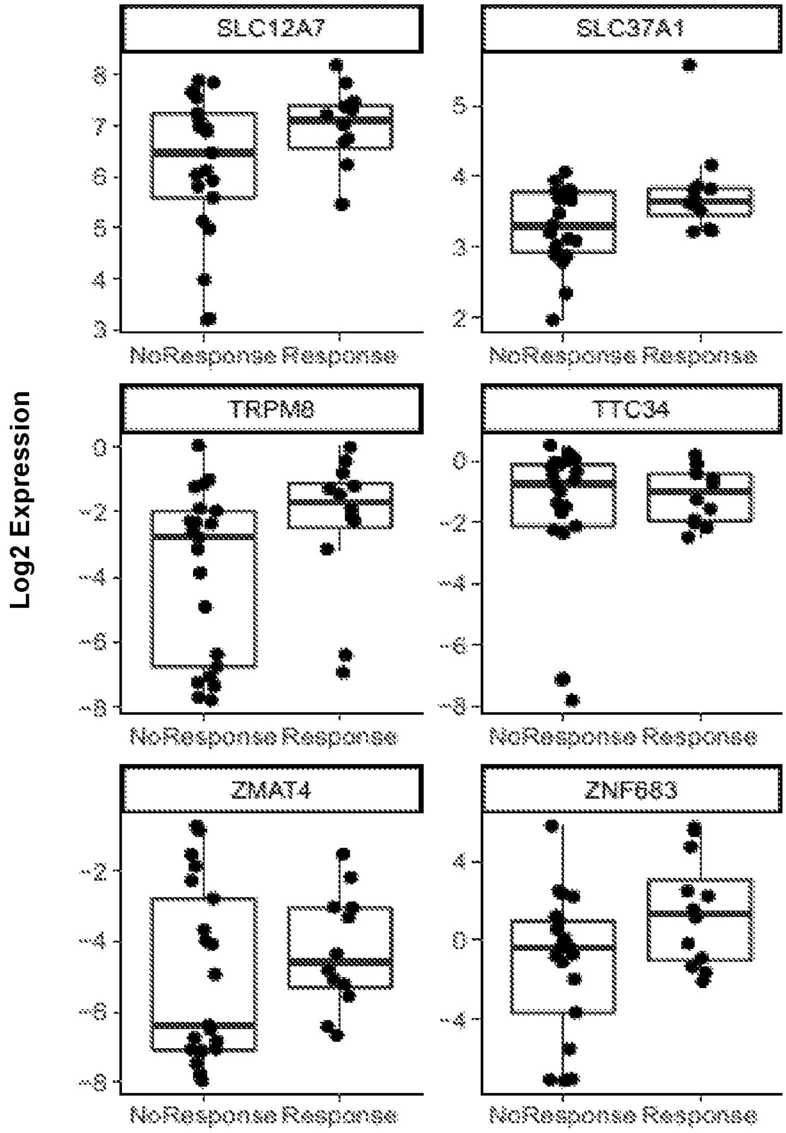
Figure 7L:
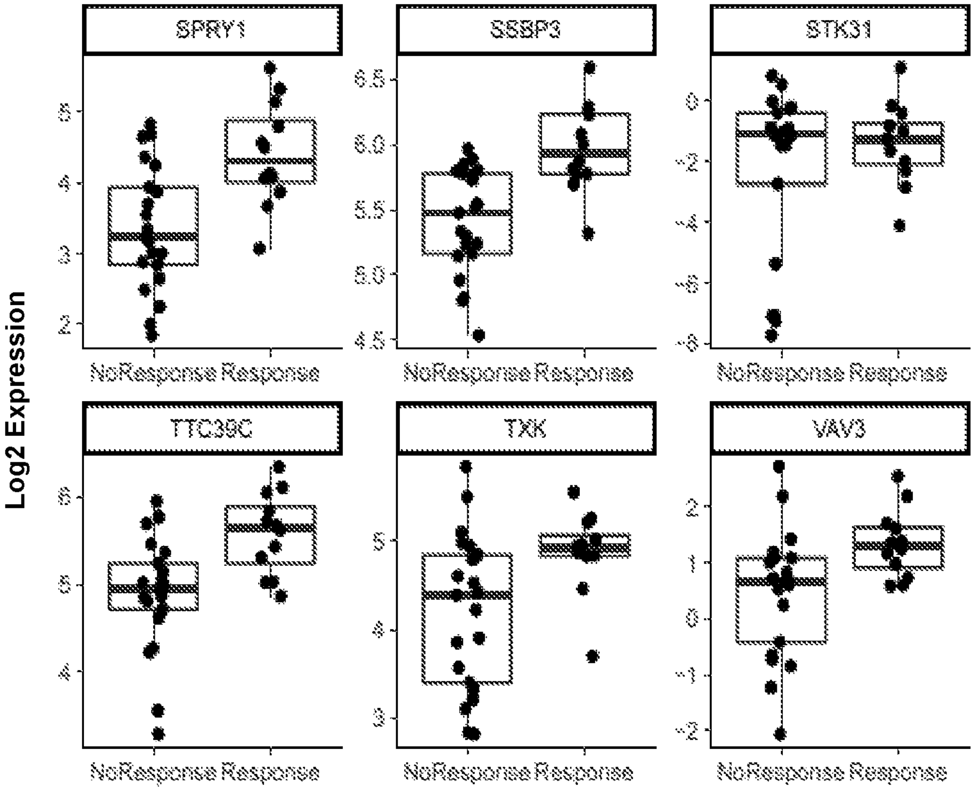
Figure 8:
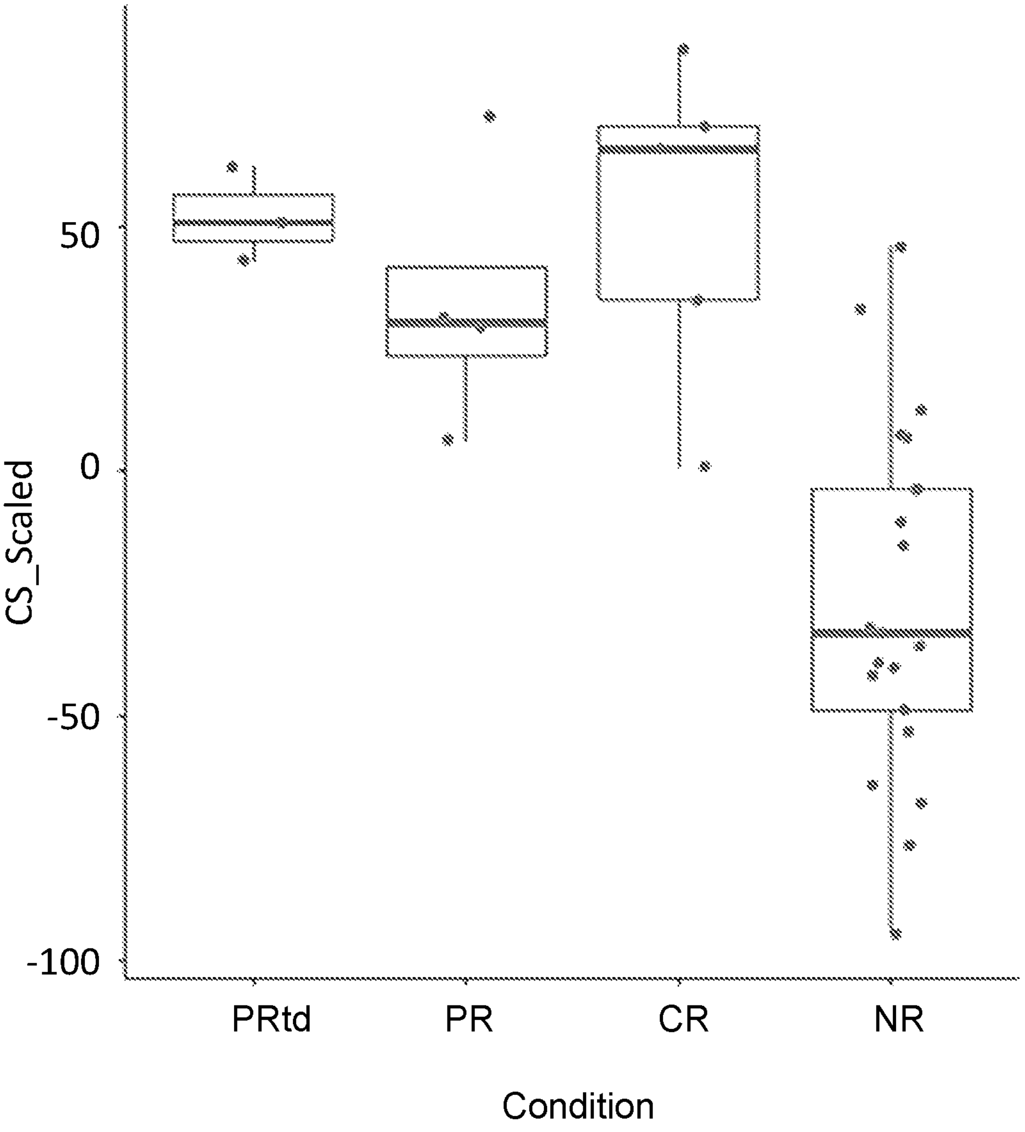
FIG. 8 is a plot showing the comparison of expression score of a limited list of target genes in the CAR T-cell products prior to infusion between patients with a Complete Response (CR), Partial Response (PR), Partial Response with transformation to aggressive B-cell lymphoma (PRtd), and No Response (NR).

As shown in FIG. 5, the developed gene expression signature correlates well with the outcome. The relative expression (Z-score) of the 107 target genes in the No Response and Response groups are shown in FIGS. 6A-6L, and the absolute expression (log 2 expression value) of the 107 target genes in No Response and Response groups are shown in FIGS. 7A-7L. The comparison of expression score of the 107 targets in FIG. 8 shows 100% of patients in the current reference dataset with a score less than or equal to zero have failed to respond to CAR T cell therapy. In this example, a diagnostic expression score greater than zero is indicative of a 70% chance of clinical response to CAR therapy.

Next, the inventors focused on a specific type of genes (transcription factors) within the list of target genes and used multinomial logistic regression to predict the response and to weight the relative importance of those transcription factors in determining if a sample will produce a good or bad clinical outcome. The analysis was expanded outside of the context of "Response" vs "No Response" to include "Partial Response" and "Complete Response". The PRtd data were combined with PR data, yielding 5 CR, 21 NR, and 7 PR. The top 25 most variable genes were first selected based on the median absolute deviation across the samples. The importance of these 25 genes were identified based on mean decrease in prediction accuracy (listed in Table 3, below). Ten-fold cross validation (training on 9/10 data set and testing on 1/10 data set) was used to assess the prediction accuracy using these 25 genes as the features. The average accuracy in this context was 0.58. However, for the two-group comparison (responder vs. non-responder), the accuracy increased to 0.83 for the same 25 genes. Importantly, in this analysis the gene selection was unbiased, i.e. no sample information (responder vs. non-responder) was used. Given the small training size and unbalanced group size, the result was considered reasonable.

TABLE 3

| Top 25 genes ranked by importance | |
|---|---|
| Gene name | Importance |
| RORA | 50.35547409 |
| EOMES | 36.70115203 |
| STAT1 | 35.8282896 |
| EGR2 | 35.00431056 |
| ASCL1 | 34.29389072 |
| BACH2 | 31.89637543 |
| E2F5 | 31.01251769 |
| ZBTB16 | 26.14435488 |
| IRF4 | 25.99010816 |
| HIC1 | 25.72321649 |
| BCL3 | 25.22608155 |
| CBFA2T3 | 24.71426408 |
| TRPS1 | 24.35677209 |
| NFKBIA | 22.88194743 |
| EGR3 | 21.76960602 |
| KLF7 | 19.79639324 |
| TCF7 | 19.69848553 |
| NR4A3 | 19.04712791 |
| SETBP1 | 18.53614676 |
| EGR1 | 18.35355323 |
| MYB | 18.26125122 |
| TFAP2A | 17.3860791 |
| BCL6 | 15.99984695 |
| LEF1 | 13.20699353 |
| NRIP1 | 4.064724136 |

A full model was then built using the entire dataset based on the expression value of the 25 featured genes. The prediction result is presented in Table 4. In the table, each value represents the probability of the patient sample falling in the corresponding group based on the overall model. The sum of each row is 1.

TABLE 4

| Prediction result using 25 featured genes | | | |
|---|---|---|---|
| Sample | No Response (NR) | Complete Response (CR) | Partial Response (PR) |
| NR.1 | 1 | 2.58E−29 | 7.41E−26 |
| NR.5 | 1 | 8.24E−11 | 5.80E−16 |
| NR.6 | 1 | 3.15E−17 | 1.34E−23 |
| NR.7 | 1 | 7.45E−41 | 6.84E−25 |
| NR.8 | 1 | 3.44E−12 | 8.99E−26 |
| NR.9 | 1 | 3.32E−48 | 1.28E−33 |
| NR.11 | 1 | 2.95E−19 | 2.13E−17 |
| NR.13 | 1 | 4.65E−45 | 2.14E−17 |
| NR.15 | 1 | 9.23E−56 | 5.61E−92 |
| NR.16 | 1 | 3.12E−28 | 1.65E−66 |
| NR.17 | 1 | 3.03E−56 | 3.35E−15 |
| NR.18 | 1 | 1.87E−37 | 7.50E−62 |
| NR.20 | 1 | 4.33E−39 | 3.86E−37 |
| NR.21 | 1 | 9.88E−29 | 6.57E−10 |
| NR.22 | 1 | 1.26E−44 | 1.22E−21 |
| NR.23 | 1 | 8.63E−10 | 1.06E−09 |
| NR.24 | 1 | 9.86E−23 | 1.40E−22 |
| NR.29 | 1 | 5.87E−18 | 1.88E−31 |
| NR.30 | 0.999951 | 4.92E−05 | 8.40E−09 |
| NR.31 | 1 | 5.85E−14 | 1.05E−38 |
| NR.33 | 1 | 6.54E−25 | 1.33E−60 |
| PR.10 | 9.05E−16 | 3.36E−42 | 1 |
| PR.19 | 1.71E−09 | 3.39E−28 | 0.999999998 |
| PR.26 | 6.14E−16 | 3.39E−21 | 1 |
| PR.28 | 2.25E−17 | 1.62E−29 | 1 |
| PRtd.12 | 1.98E−14 | 1.91E−27 | 1 |
| PRtd.14 | 9.66E−31 | 9.97E−33 | 1 |
| PRtd.32 | 7.24E−06 | 7.51E−34 | 0.999992756 |
| CR.2 | 5.12E−35 | 1 | 1.02E−25 |
| CR.3 | 1.06E−14 | 0.999999856 | 1.44E−07 |
| CR.4 | 2.86E−14 | 1 | 7.18E−28 |
| CR.25 | 3.18E−14 | 1 | 5.12E−14 |
| CR.27 | 1.80E−32 | 1 | 6.48E−35 |

Example 3. Microarray Analysis

Figure 12:
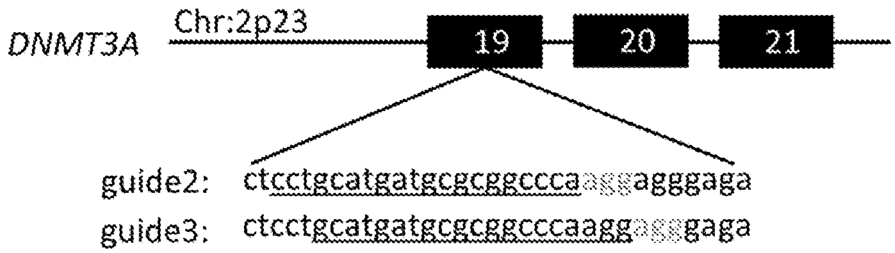
FIG. 12 shows the guide RNAs used to knockout DNMT3A. Guide 2 and guide 3 comprise the nucleotide sequence of SEQ ID NO: 1 and SEQ ID NO: 2, respectively.

Multiple DNMT3A-knockout and a "control" knockout CAR T cell lines were generated and stimulated with IL-15 multiple times. The DNMT3A knockout and control knockout CART cells were generated as follows: Peripheral blood mononuclear cells (PBMC) were isolated from consented healthy donors (IRB XPD15-086) via density gradient separation using Lymphoprep (StemCell Technologies, Vancouver, BC). Cells were then plated in 24 well non tissue culture-treated plates pre-coated with 250 ng each of anti-CD3 and anti-CD28 monoclonal antibodies (Miltenyi Biotec, Bergisch Gladbach, Germany). Culture medium for initial stimulation was RPMI 1640 supplemented with 10% fetal bovine serum and 2 mmol/L GlutaMAX (Thermo Fisher, Waltham, MA). IL-7 and IL-15 were added at 10 ng/mL and 5 ng/mL, respectively, 24 hours later. The following day, cells were transduced on RetroNectin (Takara Bio, Mountain View, CA)-coated plates and after 24 hours electroporated with *S. pyogenes* Cas9-single guide RNA RNP complexes targeting DNMT3A or mCherry (Control; MC19). Guide RNAs were purchased from Synthego (Menio Park, CA) and recombinant Cas9 was purchased from the Macro Lab at the University of California, Berkeley. Two DNMT3A-specific sgRNA sequences (guide 2 and guide 3) were used which target the catalytic domain (exon 19) (Liao J et al., Nat Genet. 2015; 47(5):469-78) of DNMT3A (see FIG. 12). Electroporation was performed using the Neon Transfection System (1600V, 3 pulses, 10 ms) according to the manufacturer's protocol (Thermo Fisher, Waltham, MA). Electroporated T-cells were left to recover in RPMI 1640 supplemented with 20% FBS, Glutamax, 10 ng/mL IL-7, and 5 ng/mL IL-15 for 72 hours. Following recovery, the media was switched to RPMI 1640 containing 10% FBS and GlutaMAX. The cells were then expanded for 10-12 days with IL-7 and IL-15 added every 2-3 days at the same concentrations indicated above. A repeat stimulation assay was performed (Krenciute G et al., Cancer immunology research. 2017; 5(7):571-81; Mata M et al., Cancer discovery. 2017; 7(11):1306-19) in which CAR T cells were cultured with tumor cells (U373) in the presence of IL15 at an effector to target (E:T) ratio of 2:1. Every 7 days, CAR T cells were counted and re-stimulated with fresh tumor cells in the presence of IL15 at the same E:T ratio (2:1), as long as CART cells had killed tumor cells at the time of T-cell harvest. For effectors, T cells expressing HER2-CAR with a CD28. endodomain (second generation CARs) or HER2-CAR with a ζ endodomain (first generation CAR) were used. mRNA was extracted from these post-stimulation cell lines and was subjected to gene expression assay by microarray. The microarray data were analyzed using standard processes (see for example, Klaus and Reisenauer, *An end to end workflow for differential gene expression using Affymetrix microarrays*. bioconductor.org, 2018) to identify differentially expressed genes between the DNMT3A-knockout and the control (MC19 knockout) cells.

The design of the experiment is shown in Table 5. In the Table, "3a2" and "3a3" indicate guide RNAs guide 2 and guide 3, respectively, targeting DNMT3A (see FIG. 12).

TABLE 5

| Experimental design | | | | |
|---|---|---|---|---|
| ID Knockout | Genotype | CAR Generation | Number of Stimulation | |

| ID | Knockout | Genotype | CAR Generation | Number of Stimulation |
|---|---|---|---|---|
| 1 | MC19 | MC19-null | First (HER2.ζ) | Fourth |
| 2 | DNMT3A | 3a2-null | First (HER2.ζ) | Fourth |
| 3 | DNMT3A | 3a3-null | First (HER2.ζ) | Fourth |
| 4 | MC19 | MC19-null | Second (HER2.CD28.ζ) | Fourth |
| 5 | DNMT3A | 3a2-null | Second (HER2.CD28.ζ) | Fourth |
| 6 | DNMT3A | 3a3-null | Second (HER2.CD28.ζ) | Fourth |
| 7 | MC19 | MC19-null | First (HER2.ζ) | Fifth |
| 8 | DNMT3A | 3a2-null | First (HER2.ζ) | Fifth |
| 9 | DNMT3A | 3a3-null | First (HER2.ζ) | Fifth |
| 10 | DNMT3A | 3a2-null | Second (HER2.CD28.ζ) | Fifth |
| 11 | MC19 | 3a3-null | Second (HER2.CD28.ζ) | Fifth |

Figure 9:
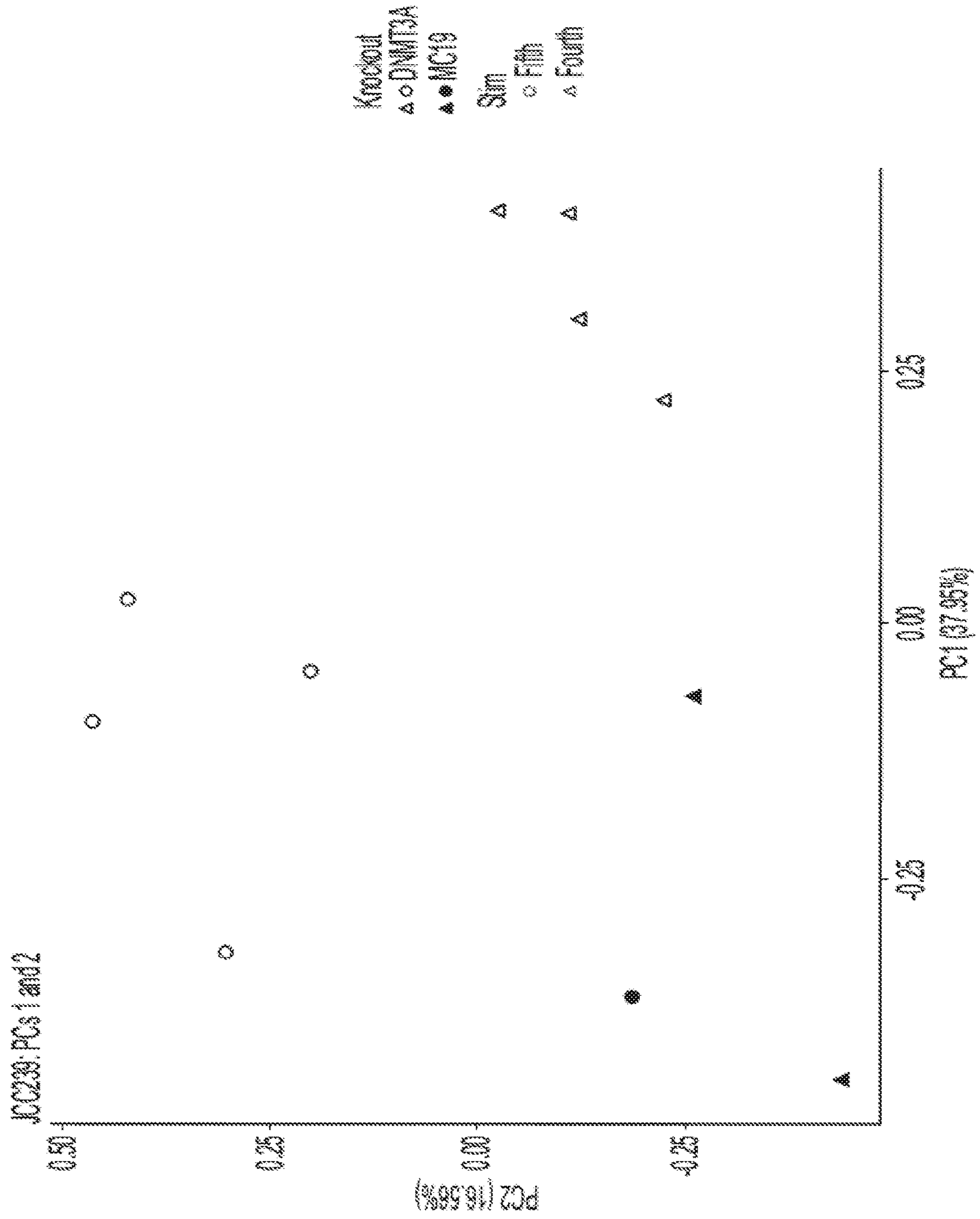
FIG. 9 is a plot showing the results of the Principal Component Analysis (PCA).

Principal component analysis (PCA) was performed to identify the key variables. Although there were a number of variables that could not be interrogated due to insufficient power, PCA analysis indicated that the majority of the variation in gene expression was explained by "Knockout" (DNMT3A vs MC19 control) and "Stimulation" (see FIG. 9).

Figure 10:
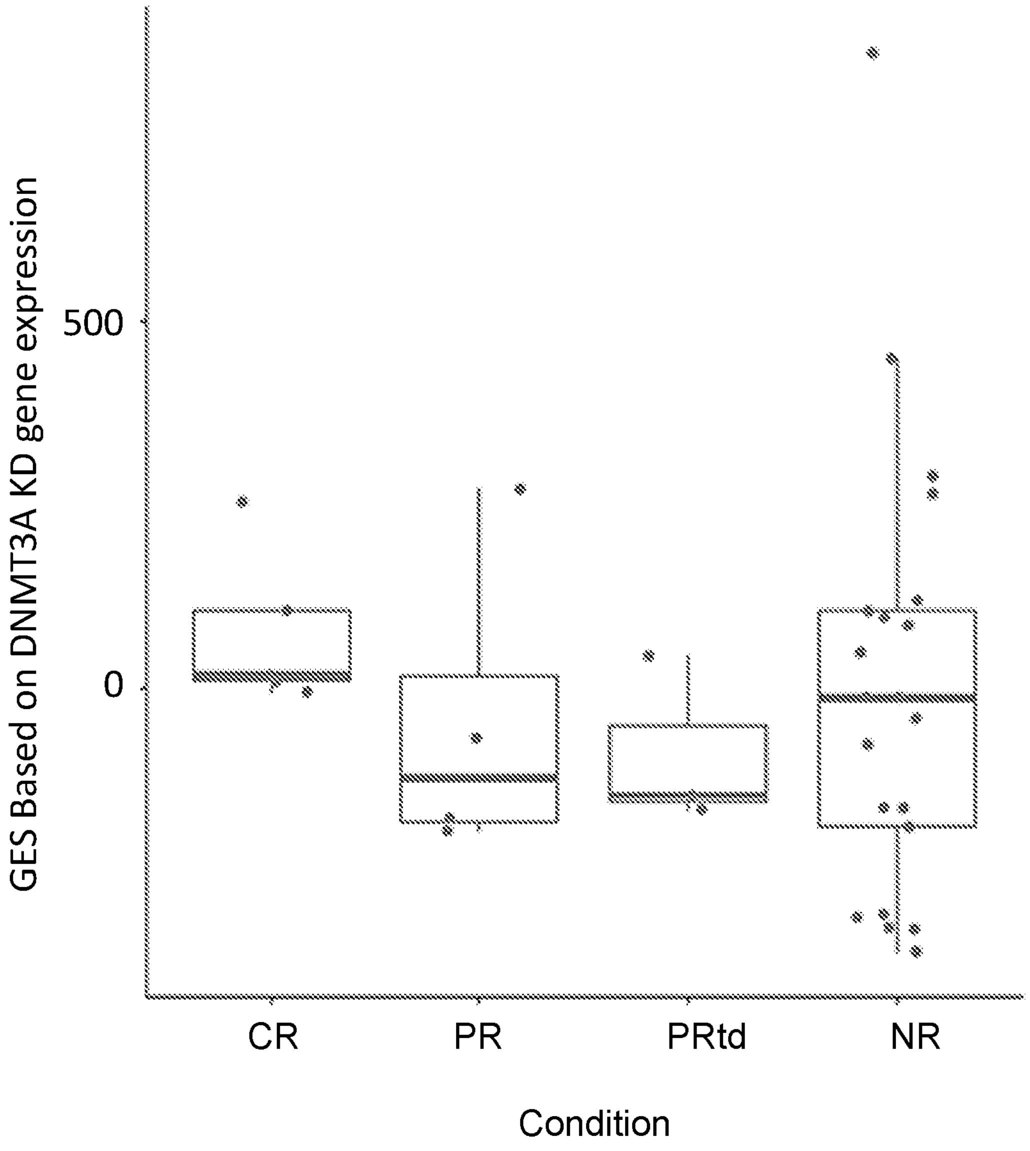
FIG. 10 is a plot showing the comparison of expression score of genes that were significantly upregulated in either Fourth Stimulation or Fifth Stimulation (or both) DNMT3A knockout CAR lines in the CAR T-cell products prior to infusion between patients with a Complete Response (CR), Partial Response (PR), Partial Response with transformation to aggressive B-cell lymphoma (PRtd), and No Response (NR).
Figure 11:
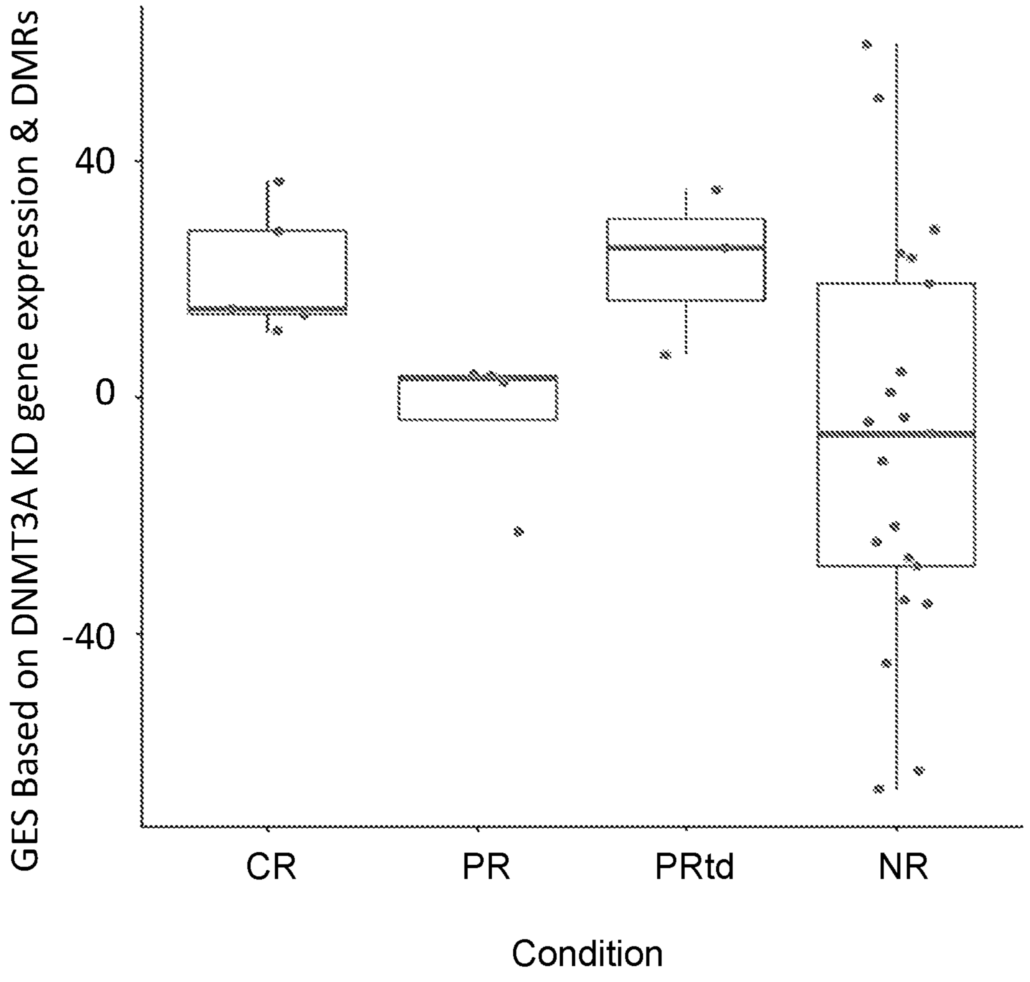
FIG. 11 is a plot showing the comparison of expression score of genes that were significantly upregulated in either Fourth Stimulation or Fifth Stimulation (or both) DNMT3A knockout CAR lines and exhibited a significant methylation difference in the CAR T-cell products prior to infusion between patients with a Complete Response (CR), Partial Response (PR), Partial Response with transformation to aggressive B-cell lymphoma (PRtd), and No Response (NR). p value between PR and CR<0.05; p value between NR and CR=0.057.

Because there was variation owed to stimulation, the data was analyzed twice, once comparing Fifth Stimulation DNMT3A-knockout to all MC19 samples, and once comparing Fourth Stimulation DNMT3A-knockout to all MC19 samples. The genes that were significantly upregulated in either Fourth Stimulation or Fifth Stimulation (or both) DNMT3A knockout CAR lines compared to control did not appear to predict patient response to CAR therapy (see FIG. 10). However, after limiting the list of differentially expressed list to only include those genes that also exhibited a significant methylation difference between DNMT3A knockout and control, patient outcome could be predicted (see FIG. 11).

These data demonstrate that only using gene expression of CAR T cells lacking DNMT3A is insufficient to determine the genes that are important for predicting CAR response; gene expression data must be integrated with or considered in the context of epigenetics (i.e., methylation targets of DNMT3A) in order to formulate accurate predictors of clinical outcome.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for predicting a subject's responsiveness to an autologous T cell therapy, said method comprising:

a) determining gene expression level of a panel of genes in a T cell sample isolated from the subject, wherein said panel of genes consists of RORA, EOMES, STAT1, EGR2, ASCL1, BACH2, E2F5, ZBTB16, IRF4, HIC1, BCL3, CBFA2T3, TRPS1, NFKBIA, EGR3, KLF7, TCF7, NR4A3, SETBP1, EGR1, MYB, TFAP2A, BCL6, LEF1, and NRIP1, b) generating a Diagnostic Expression Score for the T cell sample isolated from the subject by calculating and summing absolute or weighted gene expression level(s) determined in step (a), or by calculating and summing relative gene expression level(s) relative to reference expression level(s) obtained using responders and non-responders in a reference dataset, c) (i) determining that the subject is not likely to respond to the autologous T cell therapy if the Diagnostic Expression Score generated in step (b) is less than a threshold score; or (ii) determining that the subject is likely to respond to the autologous T cell therapy if the Diagnostic Expression Score generated in step (b) is greater than the threshold score, and d) (i) if the subject is determined in step (c) as not likely to respond to the autologous T cell therapy, (1) improving the subject's T cell functioning in T cell therapies by inhibiting DNMT3A-mediated de novo DNA methylation and/or activating STAT5 signaling pathway in the subject's T cells, and/or (2) administering to the subject an alternative therapy which is not a T cell therapy, wherein the alternative therapy is selected from antiviral therapies, bone marrow transplant, chemotherapies, checkpoint blockade, and any combinations thereof, and/or (3) administering to the subject an allogeneic T cell therapy, or (ii) if the subject is determined in step (c) as likely to respond to the autologous T cell therapy, using the subject's T cells for the autologous T cell therapy.

2. The method of claim 1, wherein the Diagnostic Expression Score is generated by Z-score summation and the threshold score is 0.

3. The method of claim 1, wherein the subject has a cancer, an infectious disease, an inflammatory disorder, or an autoimmune disease.

4. The method of claim 1, wherein inhibiting DNMT3A-mediated de novo DNA methylation in the subject's T cells is achieved by inhibiting enzymatic activity of DNMT3A protein or making DNMT3A gene deleted or defective.

5. The method of claim 4, wherein the enzymatic activity of the DNMT3A protein is inhibited by exposing the cell to a DNMT3A active site inhibitor, or the DNMT3A gene is mutated in DNMT3A catalytic domain so that the enzymatic activity of the DNMT3A protein is inhibited.

6. The method of claim 1, wherein the STAT5 signaling pathway is activated by stimulating the T cell with a signaling molecule, genetically modifying the T cell to express a signaling molecule, or by modifying the T cell to express a constitutively active cytokine receptor or a switch receptor.

7. The method of claim 6, wherein the signaling molecule is a common gamma chain cytokine.

8. The method of claim 7, wherein the cytokine is IL-15, IL-7, IL-2, IL-4, IL-9, or IL-21.

9. The method of claim 6, wherein the constitutively active cytokine receptor is a constitutively active IL7 receptor (C7R).

10. The method of claim 6, wherein the switch receptor is an IL-4/IL-7 receptor or an IL-4/IL-2 receptor.

11. The method of claim 1, wherein said improving the subject's T cell functioning is conducted ex vivo or in vitro.

12. The method of claim 1, further comprising repeating the method of claim 1 on the subject's T cells which were treated to improve the subject's T cell functioning.

13. The method of claim 1, comprising stimulating the T cells in vitro or ex vivo prior to step (a).

14. The method of claim 13, wherein the T cells are stimulated using anti-CD3 and anti-CD28 stimulation.

15. The method of claim 1, further comprising banking the subject's T cells.

16. The method of claim 1, wherein the T cell is selected from a CD8+ T cell, a CD4+ T cell, a cytotoxic T cell, an αβ T cell receptor (TCR) T cell, a natural killer T (NKT) cell, a γδ T cell, a memory T cell, a T-helper cell, and a regulatory T cell (Treg).

17. The method of claim 1, wherein the T cell therapy is a CAR T cell therapy, an αβ TCR therapy, a γδ TCR therapy, an iNKT therapy, a tumor-infiltrating lymphocyte (TIL) therapy, an in vitro sensitized (IVS) T cell therapy, or an in vivo T cell therapy.

* * * * *

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ctcctgcatg atgcgcggcc caaggaggga ga                                32


<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

ctcctgcatg atgcgcggcc caaggaggga ga                                32
```